US012758479B2

(12) United States Patent
Pouletty et al.

(10) Patent No.: US 12,758,479 B2
(45) Date of Patent: Oct. 13, 2026

(54) ADHESIVE PHOTOPROTECTIVE COMPOUNDS AND USES THEREOF

(71) Applicant: SKINOSIVE, Paris (FR)

(72) Inventors: Philippe Pouletty, Paris (FR); Denis Carniato, Marcoussis (FR); Isabelle Rault, Bourgoin-Jallieu (FR)

(73) Assignee: SKINOSIVE, Paris (FR)

(*) Notice: Subject to any disclaimer, the term of this patent is extended or adjusted under 35 U.S.C. 154(b) by 706 days.

(21) Appl. No.: 17/785,437

(22) PCT Filed: Dec. 18, 2020

(86) PCT No.: PCT/EP2020/086955
§ 371 (c)(1),
(2) Date: Jun. 15, 2022

(87) PCT Pub. No.: WO2021/123116
PCT Pub. Date: Jun. 24, 2021

(65) Prior Publication Data

US 2023/0087008 A1 Mar. 23, 2023

(30) Foreign Application Priority Data

Dec. 19, 2019 (EP) .................................... 19306696

(51) Int. Cl.
*A61Q 19/08* (2006.01)
*A61K 8/49* (2006.01)
*A61Q 17/04* (2006.01)

(52) U.S. Cl.
CPC .......... *A61K 8/4913* (2013.01); *A61K 8/4926* (2013.01); *A61K 8/496* (2013.01); *A61K 8/4973* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 5,087,445 | A | 2/1992 | Haffey et al. | |
| 5,877,204 | A | 3/1999 | Davison et al. | |
| 8,106,108 | B2 | 1/2012 | Chen | |
| 9,289,631 | B2 | 3/2016 | Musa et al. | |
| 2009/0060852 | A1* | 3/2009 | DeJovin | A61Q 17/04 514/249 |
| 2009/0156485 | A1* | 6/2009 | Barg | A61K 8/64 548/546 |
| 2014/0275482 | A1* | 9/2014 | Polukhtin | C07D 225/08 548/542 |
| 2017/0247384 | A1 | 8/2017 | Staegemann et al. | |
| 2023/0323028 | A1 | 10/2023 | Pouletty et al. | |

FOREIGN PATENT DOCUMENTS

| | | |
|---|---|---|
| AU | 2015252336 | 11/2015 |
| CH | 484 695 | 1/1970 |
| CN | 110078711 | 8/2019 |
| DE | 10 2007 024 347 A1 | 11/2008 |
| FR | 2841131 | 12/2003 |
| WO | WO 95/30646 | 11/1995 |
| WO | WO 2006/044826 | 4/2006 |
| WO | WO 2007/061232 | 5/2007 |
| WO | WO 2008/107347 | 9/2008 |
| WO | WO 2015/165710 | 11/2015 |
| WO | WO 2015/193104 | 12/2015 |
| WO | WO 2017/087894 | 5/2017 |
| WO | WO 2017/198806 | 11/2017 |

OTHER PUBLICATIONS

Wang, H. et al. "A Dual-Targeted Organic Photothermal Agent for Enhanced Photothermal Therapy" *Angew. Chem. Int. Ed.*, 2019, pp. 1057-1061, vol. 58, No. 4.

Wang, T. et al. "Design and synthesis of tumor-targeting theranostic drug conjugates for SPECT and PET imaging studies" *Bioorganic Chemistry*, 2018, available online Dec. 11, 2017, pp. 458-467, vol. 76.

Written Opinion in International Application No. PCT/EP2020/086955, Feb. 12, 2021, pp. 1-10.

* cited by examiner

*Primary Examiner* — Sahana S Kaup
*Assistant Examiner* — Ashlee E Wertz
(74) *Attorney, Agent, or Firm* — SALIWANCHIK, LLOYD & EISENSCHENK

(57) ABSTRACT

The present invention relates to a compound represented by the following formula (I): $A[B-(C)_v]_w$, wherein A is a photoprotective moiety, B is a linker, C is a functional group, v is an integer from 1 to 2000, and w is an integer from 1 to 6. It also relates to a composition comprising the same and, more particularly, to a cosmetic or a sunscreen composition. It also relates to the use of such compounds in cosmetic and therapeutic applications. The invention also relates to the use of such compounds for reducing photodegradation and/or photoinstability of pharmaceuticals and cosmetics. The invention further relates to a material comprising a support and such a compound adhered to said support.

11 Claims, No Drawings

ADHESIVE PHOTOPROTECTIVE COMPOUNDS AND USES THEREOF

CROSS-REFERENCE TO RELATED APPLICATION

This application is the U.S. national stage application of International Patent Application No. PCT/EP2020/086955, filed Dec. 18, 2020.

TECHNICAL FIELD

The present invention relates to photoprotective compounds having adhesive properties. It also relates to a composition comprising the same and, more particularly, to a cosmetic or a sunscreen composition. It also relates to the use of such compounds in cosmetic and therapeutic applications. The invention also relates to the use of such compounds for reducing photodegradation and/or photoinstability of pharmaceuticals and cosmetics. The invention further relates to a material comprising a support and such a compound adhered to said support.

TECHNICAL BACKGROUND

Almost 5% of the electromagnetic energy of the sun is emitted in the form of UV light. This UV light can be divided into three groups: UV-A (400-315 nm), UV-B (315-280 nm) and UV-C (280-100 nm). UV light, and more particularly UV-B light, can have damaging short-term or long-term effects on the body. Serious skin damages may occur due to an exposure to UV light, such as an accelerated skin ageing or a skin cancer. As a result, the development of new sunscreens providing effective protection throughout the whole UV radiation spectrum has become a prime concern and a major issue. Many sunscreens are nowadays available on the market. Despite an undeniable efficacy, it has been demonstrated that active agents of these sunscreens can penetrate through the skin into epidermal cells, and have also been detected in urine or breast milk. Small and non-adhesive nanoparticles have been developed for sunscreen compositions and are currently available on the market. However, such materials have also proven to be skin-penetrating. Bioadhesive particles have also been designed to adhere to the skin and to encapsulate active agents, such that neither the particles nor the active agents penetrate the skin. However, such bioadhesive particles are prepared by complex and costly manufacturing processes.

Therefore, there remains a need to produce efficient adhesive photoprotective compounds, which can be easily produced.

SUMMARY OF THE INVENTION

In this context, the inventors have developed photoprotective compounds comprising a photoprotective moiety and functional group(s), both being linked to each other through a linker. The functional group(s) allows the photoprotective compound to be adhesive, and more particularly bioadhesive. The photoprotective compound can interact, through its functional group(s), with any support such as a biological, organic and/or inorganic support, which makes it particularly efficient in the photoprotection field. In particular, a compound according to the invention can be used in cosmetic or therapeutic applications, such as treating or preventing skin and mucosal diseases or conditions, or reducing photodegradation and/or photoinstability of a pharmaceutical active ingredient or a cosmetic.

The present invention thus relates to a compound represented by the following formula (I):

$$A[B—(C)_v]_w, \qquad (I)$$

wherein:

A is a photoprotective moiety,

B is a linker,

C is a functional group, v is an integer from 1 to 2000, and w is an integer from 1 to 6.

In a particular embodiment, the photoprotective moiety A is derived from a UV filter and/or a SPF booster. Preferably, the photoprotective moiety A is derived from bemotrizinol, diethylamino hydroxybenzoyl hexyl benzoate, bisdisulizole disodium, meradimate, terephtalylidene dicamphor sulfonic acid, bisoctrizole, oxybenzone, sulisobenzone, iscotrizinol, octinoxate, octisalate, octyltriazone, padimate O, homosalate, amiloxate, octocrylene, PEG-25 PABA, ensulizole, trolamine salicylate, cinoxate, benzophenone-9, dioxybenzone, avobenzone, enzacamene, diethylhexyl naphthalate, diethylhexyl syringylidene, tetramethylhydroxy piperidinol, sodium benzotriazolyl butylphenol sulfonate, benzotriazole dodecyl p-cresol sulfonate, polyester-8, acrylates copolymer, butyloctyl salicylate, bis(cyano butylacetate) anthracenediylidene, dimethylcapramide, or ethyl hexyl methoxycrylene. More preferably, the photoprotective moiety A is derived from bemotrizinol, diethylamino hydroxybenzoyl hexyl benzoate, terephtalylidene dicamphor sulfonic acid, sulisobenzone, octisalate, octocrylene, ensulizole, avobenzone, polyester-8, bisdisulizole disodium, meradimate, oxybenzone-3, iscotrizinol, octanoate, octyltriazone, padimate O, cinoxate, benzophenone-9, or dioxybenzone. Even more preferably, the photoprotective moiety A is derived from bemotrizinol, diethylamino hydroxybenzoyl hexyl benzoate, terephtalylidene dicamphor sulfonic acid, or octocrylene.

In a particular embodiment, the linker B is a linear polymer, a branched polymer, a hyperbranched polymer, a dendrimer, or a residue thereof. In a more particular embodiment, the linker B further comprises at least one $—S(O)_2—$ group.

In another particular embodiment, the linker B is represented by the following formula (II):

$$—[Y—(CH_2)_q—(O—CH_2—CH_2)_p—Z—(CH_2)_s]_k—, \qquad (II)$$

wherein:

- Y is selected from —O—, —NH—, and —C(O)—;
- q is an integer from 0 to 35, preferably from 0 to 12, more preferably from 0 to 6;
- with the proviso that, when Y is —O—, q is different from 0;
- p is an integer from 0 to 250, preferably from 0 to 50, more preferably from 0 to 12; and
- p+q is different from 0; or
- $Y—(CH_2)_q$ may form a heterocycle selected in the group consisting of a pyrrolidinyl and piperidinyl; and
- p is 0;
- Z is selected from a single bond, —NH—, —O—, —NH—C(O)—, —S—, and $—S(O)_2—$;
- s is an integer from 0 to 6; and
- k is an integer from 1 to 4, preferably from 1 to 2.

In a preferred embodiment, Z is selected from —NH—, —O—, —NH—C(O)—, —S—, and $—S(O)_2—$. In a more preferred embodiment, Z is $—S(O)_2—$.

In a particular embodiment, the functional group C is chosen from an aldehyde, an acetal, thiocetal, a thiol, a maleimide, a Mickael acceptor, a vinylsulfone, a disulfanylpyridine, a sulfonylaziridine, an epoxide, a haloacetyl, an isocyanate, an isothiocyanate, a N-hydroxysuccinimide ester, a N-hydroxysulfosuccinimide ester, a hydroxy, an amino, an ammonium, a guanidinium, an imidocarbonate, a carboxylic acid, a carboxylic ester, an anhydride, a sulfonic acid, folic acid, biotin, streptavidin, avidin, antibodies, and single chain antibodies or fragments thereof, and derivatives thereof. Preferably, the functional group C is chosen from a thiol, an acetal, a maleimide, a vinylsulfone, a disulfanylpyridine, a guanidinium, folic acid, biotin, and derivatives thereof, more preferably C is a maleimide or a derivative thereof.

In a particular embodiment, the moiety B-$(C)_y$ is represented by one of the following formulae:

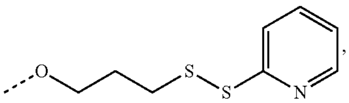,
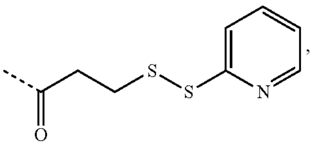,
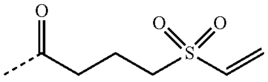,
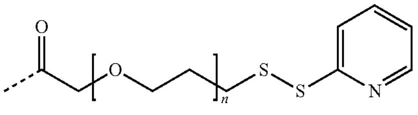,
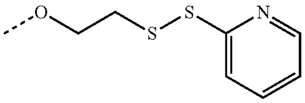,
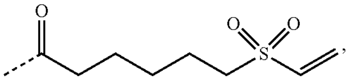,
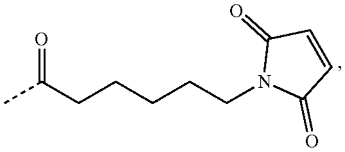,
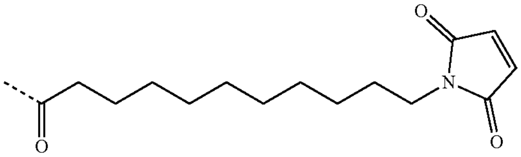,
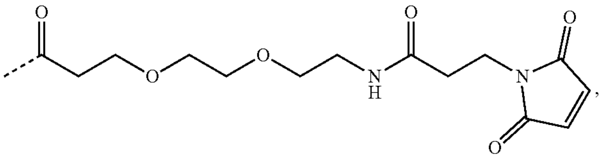,
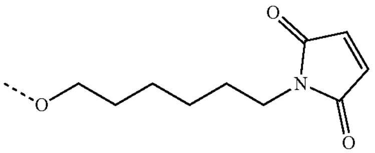,
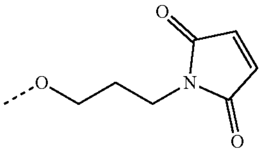,
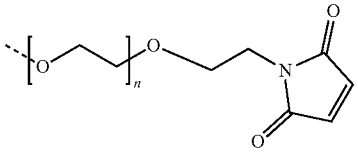,
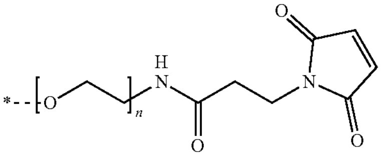,
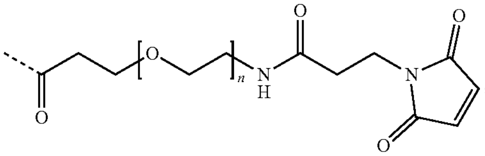,
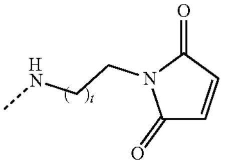,
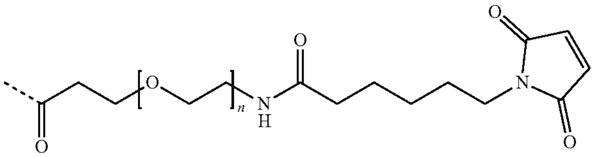,
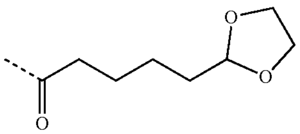,
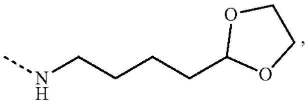,
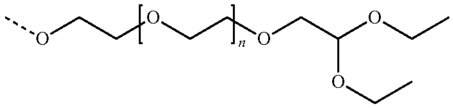,
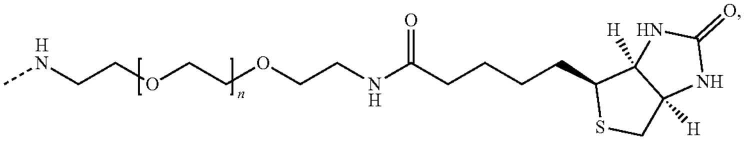, -continued
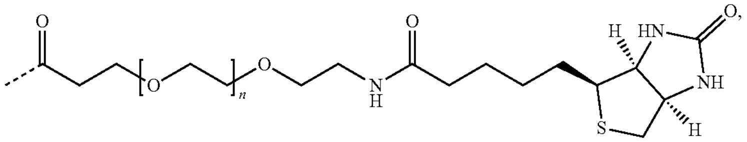
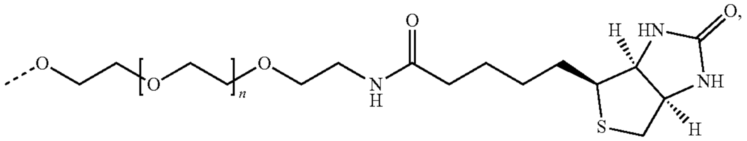
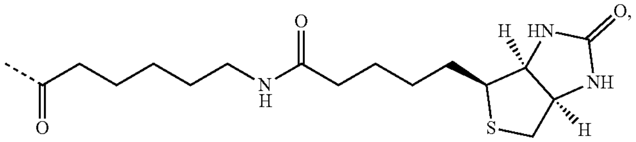
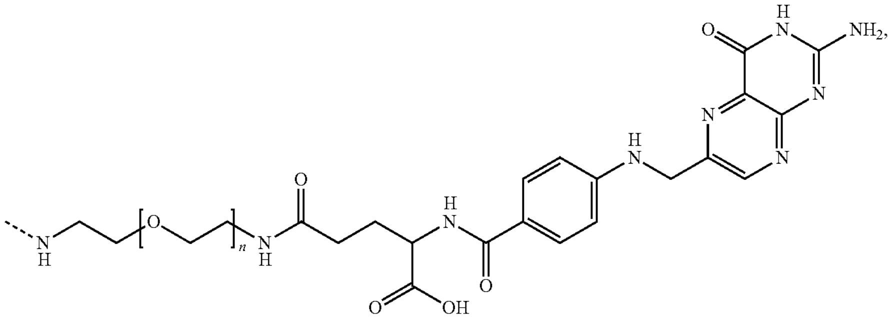
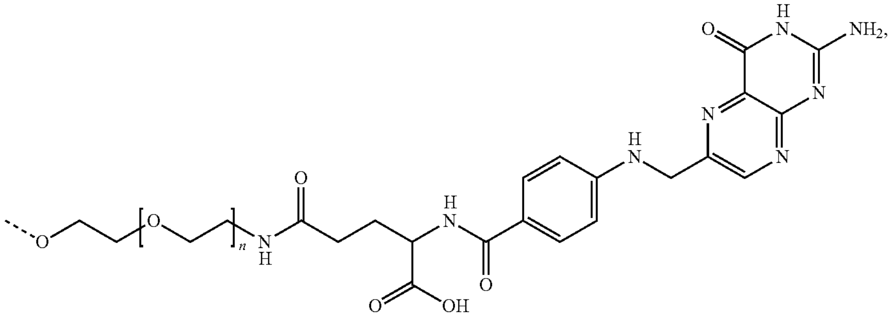
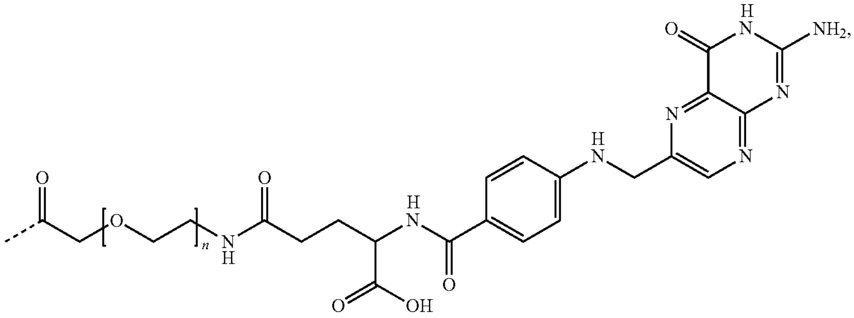
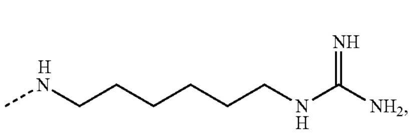
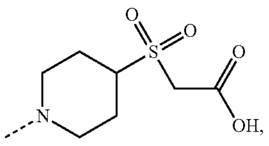
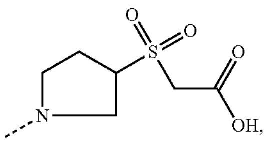
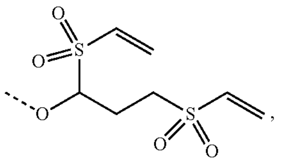
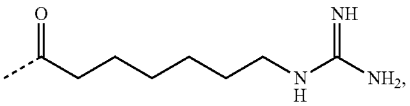
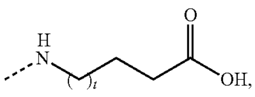 or -continued

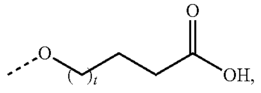

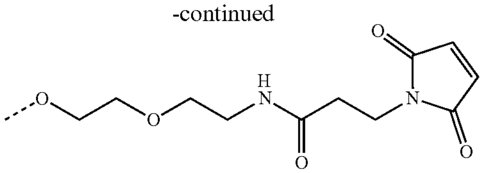

,

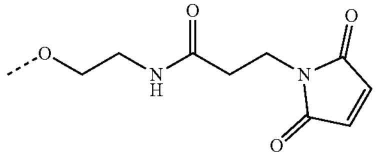

,

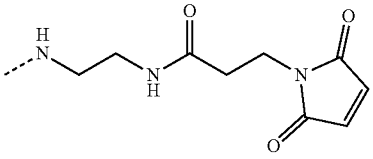

,

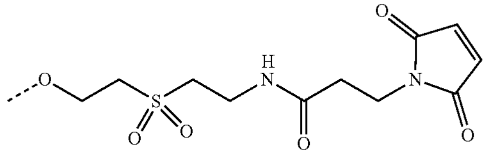

,

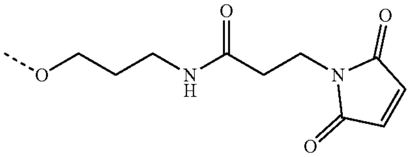

, or

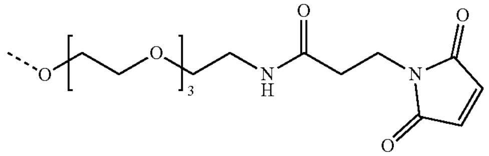

, wherein, in each formula, n is independently an integer from 0 to 250, preferably from 0 to 50, more preferably from 0 to 12, and t is independently an integer from 0 to 30, preferably from 0 to 12.

In a particular embodiment, the compound according to the invention is selected from the group consisting of:

2,2'-[6-(4-Methoxyphenyl)-1,3,5-triazine-2,4-diyl]bis[5-[(3-propyl-1H-pyrrole-2,5-dione) oxy]phenol];

2-[4-(diethylamino)-2-hydroxybenzoyl]-benzoic acid, 6-maleimido-1-hexanol ester;

2-[4-(diethylamino)-2-hydroxybenzoyl]benzoic acid, 2-(2-pyridinyldisulfanyl)ethanol ester;

2-[4-(diethylamino)-2-hydroxybenzoyl]benzoic acid, N-[5-(-2,5-dihydro-1H-pyrrole-2,5-dione)pentyl]amide;

2-[4-(diethylamino)-2-hydroxybenzoyl]benzoic acid, N-[4-(1,3-dioxolan-2-yl)butane] amide;

2-[4-(diethylamino)-2-hydroxybenzoyl]benzoic acid, biotine-PEG2-amide;

N-[4-(-2,5-dihydro-1H-pyrrole-2,5-dione)butyl]salicylamide;

2-Cyano-3,3-diphenylpropenoic acid, 6-maleimido-1-hexanol ester;

2-Cyano-3,3-diphenylpropenoic acid, folate-PEG-1k ester;

2-Cyano-3,3-diphenylpropenoic acid, 1,3-Bis(vinylsulfonyl)-1-propanol ester;

2-Phenyl-1H-benzimidazol-5-(biotine-PEGS-N-ethyl)sulfonamide;

2-Hydroxy-4-methoxybenzophenone-5-(biotine-PEG8-N-ethyl)sulfonamide;

[N-(2-Cyano-3,3-diphenylpropenoyl)-piperidin-4-ylsulfonyl]acetic acid;

N-[(2-hydroxybenzoyl)-piperidin-4-ylsulfonyl]acetic acid;

(3-(2H-benzo[d][1,2,3]triazol-2-yl)-5(tert-butyl)-4-hydroxyphenyl)propanoic, N-[(4-piperidin-4-ylsulfonyl) acetic] amide;

2-[4-(diethylamino)-2-hydroxybenzoyl]-benzoic acid, 2-[2-[3-(2,5-dioxopyrrol-1-yl) propanoylamino]ethoxy]ethyl ester;

2-[4-(diethylamino)-2-hydroxy-benzoyl]benzoic acid, 2-[3-(2,5-dioxopyrrol-1-yl)propanoylamino]ethyl ester;

2-cyano-N-[2-[3-(2,5-dioxopyrrol-1-yl)propanoylamino]ethyl]-3,3-diphenyl-prop-2-enamide;

2-cyano-3,3-diphenyl-prop-2-enoate, 2-[2-[3-(2,5-dioxopyrrol-1-yl)propanoylamino]ethylsulfonyl]ethyl ester;

3-(2,5-dioxopyrrol-1-yl)-N-[2-[[(3Z)-3-[[4-[(Z)-[4-[2-[3-(2,5-dioxopyrrol-1-yl)propanoyl amino]ethylsulfamoylmethyl]-7,7-dimethyl-3-oxo-norbornan-2-ylidene]methyl] phenyl] methylene]-7,7-dimethyl-2-oxo-norbornan-1-yl] methylsulfonylamino] ethyl]propenamide;

3-(2,5-dioxopyrrol-1-yl)-N-[3-[4-[4-[4-[3-[3-(2,5-dioxopyrrol-1-yl)propanoylamino]propoxy]-2-hydroxy-phenyl]-6-(4-methoxyphenyl)-1,3,5-triazin-2-yl]-3-hydroxy-phenoxy]propyl]propenamide; and 3-(2,5-dioxopyrrol-1-yl)-N-[2-[2-[2-[2-[4-[4-[4-[2-[2-[2-[2-[3-(2,5-dioxopyrrol-1-yl)propanoylamino]ethoxy]ethoxy]ethoxy]ethoxy]-2-hydroxy-phenyl]-6-(4-methoxyphenyl)-1,3,5-triazin-2-yl]-3-hydroxy-phenoxy]ethoxy]ethoxy]ethoxy]ethyl]propanamide.

It also relates to a composition comprising at least one compound of formula (I) as defined herein and at least one excipient. In a particular embodiment, said composition is a sunscreen composition or a cosmetic composition. In another particular embodiment, said composition is a pharmaceutical or a veterinary composition.

A further object of the present invention is a cosmetic use of a composition as defined herein, for combatting and/or reducing the signs of cutaneous ageing, such as the formation of wrinkles and/or fine lines, skin sagging, loss of firmness, loss of radiance and/or evenness of the complexion, and/or for reinforcing the skin barrier.

Another object of the present invention is a cosmetic process for combatting and/or reducing the signs of cutaneous ageing, such as the formation of wrinkles and/or fine lines, skin sagging, loss of skin firmness, loss of radiance and/or evenness of the complexion, and/or for reinforcing the skin barrier, comprising applying topically to the skin, a composition as defined herein.

Another object of the present invention is a kit comprising:

a composition as defined herein, a washing composition, preferably a powder, a shampoo, a soap, a lotion, a solution, a solid, a scrubbing, a scraper, a mousse, a foam, a syndet, a gel, a shower gel, a spray, a mist, a wax, a strip, an enzyme composition, a detergent composition, or a woven or non-woven fabric, and, optionally an instruction guide.

The present invention also relates to a composition as defined herein, for use for treating and/or preventing a skin, mucosa, eye cornea, or skin appendage disease or condition. Preferably, said skin, mucosa, eye cornea, or skin appendage disease or condition is chosen from lipodystrophy, keloid scars, acne, psoriasis, atopic dermatitis, actinic keratosis, rosacea, melasma, melanoma, Merker cell carcinoma, basal cell carcinoma, squamous cell carcinoma, scar treatments, wound healing, alopecia, vitiligo, urticaria (hives), cold sores, impetigo, eczema, rashes dermatitis, ichthyosis, warts, blisters, pruritus, gangrene, bruises, pustules, bacterial skin infections like leprosy, carbuncles, cellulitis, impetigo, fungal infections like Athlete's foot (intertrigo) and sporotrichosis, fungal nail infections, viral infection like herpes, sunburns, lice, scabies, pressure ulcer disinfection, and pressure ulcer healing.

In a particular embodiment, a composition as defined herein or a composition for use as defined herein is a topical composition. In a more particular embodiment, a composition as defined herein or a composition for use as defined herein is in the form of a suspension, a cream, a spray, an aerosol, a butter, a stick, a gel, an ointment, a lotion, a solution, a solid, an emulsion, a micro-emulsion, an oil, a lyophilizate, a milk, a powder, a paste, a wax, a mousse, a patch, a film, a micelle, a liposome, or a foam.

The present invention also relates to a use of at least one compound of formula (I) as defined herein for reducing photodegradation and/or photoinstability of a pharmaceutical active ingredient or a cosmetic. In this particular application, said at least one compound is in a form of a micelle or a liposome.

Another object of the invention is a material comprising a support and at least one compound of formula (I) as defined herein, said compound being adhered to said support. Preferably, said support is a natural or synthetic polymeric support, a natural or synthetic fiber support, a stone, a metal, a plastic, a rubber or a glass support.

DETAILED DESCRIPTION OF THE INVENTION

Photoprotective Compound

The present invention relates to a compound comprising a photoprotective moiety, functionalized with at least one functional group, which is linked to the photoprotective moiety through at least one linker. The linker(s) may linear, branched, hyperbranched, or dendritic, and may be polymeric or not. The functional group is able to render the compound of the invention adhesive, preferably bioadhesive.

A compound of the invention is typically represented by the following formula (I):

$$A[B\text{—}(C)_v]_w, \quad (I)$$

wherein:

A is a photoprotective moiety,

B is a linker,

C is a functional group, v is an integer from 1 to 2000, and w is an integer from 1 to 6.

A compound of formula (I) according to the invention thus comprises a photoprotective moiety A linked to at least one linker B (w), having at least one functional group C (v).

As used herein, w represents the number of groups $[B-(C)_v]$ linked to the photoprotective moiety A. According to the invention, w is an integer from 1 to 6. In other words, the photoprotective moiety A is linked to 1 to 6 linkers B. For instance, when w is 3, the photoprotective moiety A is linked to 3 linkers B.

In a particular embodiment, w is an integer from 1 to 4, preferably from 1 to 3, and more preferably w is 1 or 2.

As used herein, v represents the number functional groups C linked to each linker B. According to the invention, v is an integer from 1 to 2000. In other words, each linker B is independently linked to 1 to 2000 functional groups C. For instance, when v is 2, the linker B comprises 2 functional groups C. In a particular embodiment, v is an integer from 100 to 1000, preferably from 150 to 500, and more preferably from 150 to 250. In another particular embodiment, v is 1 or 2, preferably 1.

The photoprotective moiety A and the linker(s) B may be linked (or "bound"), covalently and/or non-covalently, for instance ionically, to each other. Preferably, the photoprotective moiety A and the linker(s) B are linked covalently to each other.

The linker(s) B and the functional group(s) C may be linked (or "bound"), covalently and/or non-covalently, for instance ionically, to each other. Preferably, the linker(s) B and the functional group(s) C are linked covalently to each other.

The Photoprotective Moiety A

According to the invention, a compound of formula (I) comprises a photoprotective moiety A. As used herein, a "photoprotective moiety" refers to a photoprotective agent deprived of one or more atoms or atom groups, wherein the photoprotective activity of the photoprotective moiety is substantially similar to that of the photoprotective agent from which it derives. A photoprotective agent is typically an organic substance which can block or absorb all or part of a light, in particular, a light that can cause damages on the subject or material to be protected, such as Ultraviolet ("UV") light. A photoprotective agent is typically a UV filter, and/or a SPF booster.

In a particular embodiment, the photoprotective moiety A is derived from a UV filter and/or a SPF booster.

In particular, a UV filter may be a UVA filter, such as a UVA I or UVA II filter, a UV B filter, or a combination thereof.

Examples of UVA I filters include, but are not limited to, bemotrizinol, diethylamino hydroxybenzoyl hexyl benzoate (DHHB), bisdisulizole disodium, meradimate, or ecamsule.

Examples of UVA II/UVB filters include, but are not limited to, oxybenzone, sulisobenzone, iscotrizinol, octinoxate, octisalate, octyltriazone, padimate O, homosalate, amiloxate, octocrylene, PEG-25 PABA, ensulizole, trolamine salicylate, cinoxate, benzophenone-9, dioxybenzone, or avobenzone.

Examples of UVA/UVB filters include, but are not limited to, enzacamene or bisoctrizole.

In particular, a SPF booster may be a T-T quencher, an Excited state quencher, or a combination thereof.

Examples of T-T quenchers include, but are not limited to, diethylhexyl naphthalate or diethylhexyl syringylidene.

Examples of Excited state quenchers include, but are not limited to, tetramethylhydroxy piperidinol, sodium benzotriazolyl butylphenol sulfonate, benzotriazole dodecyl p-cresol sulfonate, polyester-8, acrylates copolymer, butyloctyl salicylate, bis(cyano butylacetate) anthracenediylidene, dimethylcapramide, or ethyl hexyl methoxycrylene.

In a particular embodiment, the photoprotective moiety A is derived from bemotrizinol, diethylamino hydroxybenzoyl hexyl benzoate (Uvinul® A Plus), bisdisulizole disodium, meradimate, terephtalylidene dicamphor sulfonic acid (also referred to as ecamsule), bisoctrizole, oxybenzone, sulisobenzone, iscotrizinol, octinoxate, octisalate, octyltriazone, padimate O, homosalate, amiloxate, octocrylene, PEG-25 PABA, ensulizole, trolamine salicylate, cinoxate, benzophenone-9, dioxybenzone, avobenzone, enzacamene, diethylhexyl naphthalate, diethylhexyl syringylidene, tetramethylhydroxy piperidinol, sodium benzotriazolyl butylphenol sulfonate, benzotriazole dodecyl p-cresol sulfonate, polyester-8, acrylates copolymer, butyloctyl salicylate, bis(cyano butylacetate) anthracenediylidene, dimethylcapramide, or ethyl hexyl methoxycrylene.

In a preferred embodiment, the photoprotective moiety A is derived from bemotrizinol, diethylamino hydroxybenzoyl hexyl benzoate, terephtalylidene dicamphor sulfonic acid, sulisobenzone, octisalate, octocrylene, ensulizole, avobenzone, polyester-8, bisdisulizole disodium, meradimate, oxybenzone-3, iscotrizinol, octanoate, octyltriazone, padimate O, cinoxate, benzophenone-9, or dioxybenzone.

In a more preferred embodiment, the photoprotective moiety is derived from bemotrizinol, diethylamino hydroxybenzoyl hexyl benzoate, terephtalylidene dicamphor sulfonic acid, or octocrylene.

In an even more preferred embodiment, the photoprotective moiety A is derived from terephtalylidene dicamphor sulfonic acid or diethylamino hydroxybenzoyl hexyl benzoate.

In a particular embodiment, the photoprotective moiety A is derived from a tris-aryltriazine. Examples of tris-aryltriazine include, but are not limited to, tris-aryltriazine compounds described in U.S. Pat. No. 8,106,108. In another particular embodiment, the photoprotective moiety A is derived from a hydroxyphenyl benzotriazole. Examples of hydroxyphenyl benzotriazole include, but are not limited to, bisoctrizole, benzenepropanoic acid, 3-(2H-benzotriazol-2-yl)-5-(1,1-dimethylethyl)-4-hydroxy-, and $C_7$-$C_9$-branched or linear alkyl esters thereof.

The Functional Group C

According to the present invention, C represents a functional group. As used herein, a "functional group" is a group that is able to react with or bound to any support of any material, any tissues, cells, intracellular or extracellular materials, making the compound of formula (I) adhesive or bioadhesive.

In a particular embodiment, the functional group C is chosen from an aldehyde, an acetal, thiocetal, a thiol, a maleimide, a Mickael acceptor, a vinylsulfone, a disulfanylpyridine, a sulfonylaziridine, an epoxide, a haloacetyl, an isocyanate, an isothiocyanate, a N-hydroxysuccinimide ester, a N-hydroxysulfosuccinimide ester, a hydroxy, an amino, an ammonium, a guanidinium, an imidocarbonate, a carboxylic acid, a carboxylic ester, an anhydride, a sulfonic acid, folic acid, biotin, streptavidin, avidin, antibodies, and single chain antibodies or fragments thereof. In a more particular embodiment, C further includes any derivatives of such functional groups as above detailed.

For instance, the term "maleimide" (Mal) refers to the maleimide group and any derivative thereof. In particular, the maleimide (Mal) includes the two following groups of formula (Mal 1) and (Mal 2):

(Mal 1)

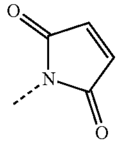

(Mal 2)

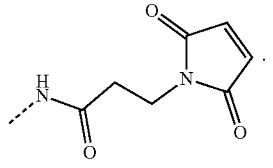

As used in the formulae disclosed in the present application, the symbol "- - - - -" in a formula represents the bond by which a moiety of said formula is attached to the remainder of the molecule. For instance, said symbol represented above in (Mal 1) or (Mal 2) represents the bond by which the moiety is attached to the linker B.

In a preferred embodiment, the functional group C is chosen from a thiol, an acetal, a maleimide, a vinylsulfone, a disulfanylpyridine, a guanidinium, folic acid, biotin, and a derivative thereof.

In a preferred embodiment, C is a maleimide (also named "Mal") or a derivative of maleimide as above disclosed. More preferably, C is Mal 1 or Mal 2.

In a further particular embodiment, C represents a native functional group.

As used herein, a "native functional group" of a polymer is a functional group which is intrinsically present in the structure of the polymer and thus has not been converted into another functional group. For instance, hydroxy groups are native functional groups of cellulose, and carboxylic acids (or carboxylate) are native functional groups of a polymethacrylic acid.

In a further particular embodiment, C represents a modified functional group.

As used herein, a "modified functional group" of a polymer is a functional group that results from the conversion of a native functional group as defined herein into another functional group, for instance, an aldehyde group resulting from oxidation of a hydroxy group of cellulose or a biotin linked to a hydroxy group of cellulose.

The Linker B

According to the invention, a compound of formula (I) comprises at least one linker B (w).

A "linker" refers to any organic chain having at least one carbon, which links the photoprotective moiety to at least one functional group. The linker B may be linear, branched, hyperbranched, or dendritic. B may be polymeric or not.

In a particular embodiment, the linker B is biodegradable.

The term "biodegradable linker (or compound)" refers to a linker (or a compound) that will degrade or erode under physical, chemical, and/or biological conditions to smaller units or chemical species that are capable of being metabolized, eliminated, or excreted by the subject. The degradation time and speed are a function of composition and/or morphology. Degradation time can be from hours to weeks.

In a particular embodiment, the linker B is a linear polymer, a branched polymer, a hyperbranched polymer, a dendrimer (or "dendritic polymer"), or a residue thereof.

As used herein, the term "linear polymer" refers to a polymer which does not have any branches. The term "branched polymer" refers to a polymer having a linear chain substituted by primary branches, and optionally secondary branches. The term "hyperbranched polymer" refers to a polymer having randomly arranged primary and secondary branches. The term "dendrimer" (also referred to as "dendritic polymer" or "dendronized polymer") refers to a repetitively branched polymer having a symmetric and organized tree-structure, in which branches originate from a common branch point. The term "residue of polymer" refers to a polymer deprived of one or more of its functional groups (such as —$NH_2$, —COOH, —OH), or atom(s) thereof (such as H or —OH).

The polymer of said linear, branched, hyperbranched, or dendritic polymer may be a homopolymer or a copolymer. The polymer of said linear, branched, hyperbranched, or dendritic polymer may be natural, semi-synthetic, hemi-synthetic, or synthetic.

The term "homopolymer" generally refers to a polymer that is composed of identical monomers.

The term "copolymer" generally refers to a polymer that is composed of two or more different monomers. The copolymer can be of any form, such as random, block, or graft. The copolymers can have any end-group.

Examples of semi-synthetic, hemi-synthetic or synthetic polymers include, but are not limited to, poly(hydroxy acids) such as poly(lactic acid), poly(glycolic acid), and poly(lactic acid-co-glycolic acid), poly(lactide), poly(glycolide), poly (lactide-co-glycolide), polyanhydrides, polyorthoesters, polyamides, polycarbonates, polyglycerol, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, hydroxypropyl methylcellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, copolymers of acrylates and ammonium methacrylate, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate) (jointly referred to herein as "polyacrylic acids"), poly(butyric acid), poly(valeric acid), and poly(lactide-co-caprolactone), copolymers and blends thereof.

Examples of natural polymers include, but are not limited to, proteins such as albumin, collagen, gelatin and prolamines (e.g. zein), and polysaccharides such as alginate, dextran, chitosan, cellulose derivatives and polyhydroxyalkanoates (e.g. polyhydroxybutyrate) and microbial anatoxins.

In a particular embodiment, the linker B further comprises at least one —$S(O)_2$— group. The —$S(O)_2$— group(s) may be at any position of the linker B. For instance, the —$S(O)_2$— group(s) may be at one or two ends of the linker B and/or may interrupt the linker B at any position. The —$S(O)_2$— group(s) advantageously improve the photoprotective properties of the compound of the invention. In particular, a higher refractive index and/or a higher transparency of the compound of the invention may be obtained.

According to the invention, the linker B is linked to at least one functional groups C (v). In an embodiment, the linker B comprises at least one residue of polymer. In such an embodiment, the functional group(s) C is(are) linked to the at least one residue of polymer of the linker B. In such an embodiment, C represents one or more functional groups of at least one residue of polymer of the linker (B).

In order to illustrate various embodiments for the moiety $[B\text{-}(C)_v]$, it is provided below different representation of the moiety $[B\text{-}(C)_v]$ based on cellulose as a polymer linker B.

- $[B\text{-}(C)_v]$ can be cellulose. In this embodiment, B represents a residue of cellulose, C represents hydroxy groups (that are native groups of cellulose), and v is the number of hydroxy groups;
- $[B\text{-}(C)_v]$ can also be aldehyde-modified cellulose. In this embodiment, B represents a residue of cellulose, C represents aldehyde groups (that are modified groups of cellulose), and v is the number of aldehyde groups;
- $[B\text{-}(C)_v]$ can also be biotin-modified cellulose. In this embodiment, B represents a residue of cellulose, C represents biotin groups (that are modified groups of cellulose), and v is the number of biotin groups.

In another particular embodiment, the linker B is represented by the following formula (II):

$$—[Y—(CH_2)_q—(O—CH_2—CH_2)_p—Z—(CH_2)_s]_k—, \quad (II)$$

wherein:

Y is selected from —O—, —NH—, and —C(O)—;

q is an integer from 0 to 35, preferably from 0 to 12, more preferably from 0 to 6;

with the proviso that, when Y is —O—, q is different from 0;

p is an integer from 0 to 250, preferably from 0 to 50, more preferably from 0 to 12; and p+q is different from 0; or Y—$(CH_2)_q$ may form a heterocycle selected in the group consisting of a pyrrolidinyl and piperidinyl; and p is 0;

Z is selected from a single bond, —NH—, —O—, —NH—C(O)—, —S—, and —$S(O)_2$—;

s is an integer from 0 to 6; and k is an integer from 1 to 4, preferably from 1 to 2.

In a further particular embodiment, the linker B is represented by the following formula (II):

$$—[Y—(CH_2)_q—(O—CH_2—CH_2)_p—Z—(CH_2)_s]_k—, \quad (II)$$

in which:

Y is selected from —O—, —NH—, and —C(O)—, preferably —O—;

q is an integer from 1 to 35, preferably from 1 to 12, more preferably from 1 to 6; and p is an integer from 0 to 250, preferably from 0 to 50, more preferably from 0 to 12; or Y—$(CH_2)_q$ may form a heterocycle selected in the group consisting of a pyrrolidinyl and piperidinyl; and p is 0;

Z is selected from a single bond, —NH—, —O—, —NH—C(O)—, —S—, and —$S(O)_2$—;

s is an integer from 0 to 6; and k is an integer from 1 to 4, preferably from 1 to 2.

In a particular embodiment, the linker B is of formula (II), in which:

Y is selected from —O—, —NH—, and —C(O)—, preferably —O—, and —NH—;

q is an integer from 0 to 12, preferably from 0 to 6;

with the proviso that, when Y is —O—, q is different from 0;

p is an integer from 0 to 50, preferably from 0 to 20; more preferably from 0 to 12; and p+q is different from 0.

In a more particular embodiment, p is 0.

In a further more particular embodiment, p is an integer from 1 to 50, more preferably from 1 to 12.

In another particular embodiment, the linker B is of formula (II), in which:

Y—$(CH_2)_q$ forms a heterocycle selected in the group consisting of a pyrrolidinyl and piperidinyl, and p is 0.

In a particular embodiment, Z is selected from a single bond, —NH—, —NH—C(O)— and —$S(O)_2$—. In a preferred embodiment, Z is a single bond. In another preferred embodiment, Z is selected from —NH—, —O—, —NH—C(O)—, —S—, and —$S(O)_2$—, more preferably Z is —$S(O)_2$—.

In a particular embodiment, s is an integer from 0 to 2, and preferably, s is 0. In another particular embodiment, s is an integer from 1 to 6.

In a particular embodiment, k is 1.

In a particular embodiment, the linker B is of formula (II), in which:

Y is selected from —O—, —NH—, and —C(O)—, preferably from —O— and —NH—;

q is an integer from 0 to 35, preferably from 0 to 12, more preferably from 0 to 6;

with the proviso that, when Y is —O—, q is different from 0;

p is an integer from 0 to 50, preferably from 0 to 12, more preferably p is 0; and p+q is different from 0; or Y—$(CH_2)_q$ may form a heterocycle selected in the group consisting of a pyrrolidinyl and piperidinyl; and p is 0;

Z is selected from a single bond, —NH—, —O—, and —$S(O)_2$—;

s is 0 or 1, preferably 0; and k is 1.

In a more particular embodiment, the linker B is of formula (II), in which:

Y is selected from —O— and —NH—;

q is an integer from 1 to 12, preferably from 1 to 6;

p is 0;

Z is a single bond;

s is 0; and k is 1.

In such an embodiment, the functional group C is preferably a disulfanylpyridine, a maleimide, a vinylsulfone, an acetal, or a derivative thereof, more preferably a maleimide or a derivative thereof.

In a further more particular embodiment, the linker B is of formula (II), in which:

Y—$(CH_2)_q$ forms a heterocycle selected in the group consisting of a pyrrolidinyl and piperidinyl; and p is 0;

Z is —$S(O)_2$—;

s is an integer from 1 to 6, preferably 1 to 3; and k is 1.

In such an embodiment, the functional group C is preferably a carboxylic acid.

In a particular embodiment, the linker B is of formula (II), in which:

Y is selected from —O— and —NH—;

q is an integer from 1 to 12, more preferably from 1 to 6;

p is an integer from 1 to 50, preferably from 1 to 12; and

Z is selected from a single bond, —NH—, —O—, and —$S(O)_2$—;

s is 0; and k is 1.

In such an embodiment, the functional group C is preferably a biotin or a folic acid.

In another particular embodiment, the linker B is of formula (II) in which:

Y is selected from —O—, —NH—, and —C(O)—;

q is an integer from 1 to 35, preferably from 2 to 12, more preferably from 2 to 4;

p is an integer from 0 to 250, preferably from 0 to 50, more preferably from 0 to 12; and; or Z is selected from —NH—, —O—, —NH—C(O)—, —S—, and —$S(O)_2$—;

s is an integer from 1 to 6; and k is 1 or 2.

In a preferred embodiment, the linker B is of formula (II), in which:

Y is selected from —O—, and —NH—;

q is an integer from 1 to 6, preferably q from 2 to 4;

p is an integer from 0 to 12, preferably from 0 to 6;

Z is selected from —NH—C(O)—, and —$S(O)_2$—, preferably —NH—C(O)—;

s is an integer from 1 to 6, preferably s is 2; and k is 1.

In such an embodiment, the functional group C is preferably a maleimide (also named “Mal”) or a derivative of maleimide as above disclosed.

In a further particular embodiment, the linker B is of formula (II) and further comprises a —$S(O)_2$— group. In such an embodiment, said —$S(O)_2$— group may be at any position of the group of formula (II). According to this particular embodiment, the linker B may be represented by the following formula (II'):

$$—[Y—(CH_2)_q—S(O)_2—(CH_2)_{q'}—(O—CH_2—CH_2)_p—Z—(CH_2)_s]_k— \quad (II'),$$

in which:

Y is selected from —O—, —NH—, and —C(O)—, preferably —O—;

q' and q" are each an integer from 0 to 35, preferably from 1 to 12, more preferably from 1 to 6;

q'+q" is comprised between 0 and 35;

with the proviso that, when Y is —O—, q'+q" is different from 0;

p is an integer from 0 to 250, preferably from 0 to 50, more preferably from 0 to 12; and p+q is different from 0; or Z is selected from a single bond, —NH—, —O—, —NH—C(O)—, —S—, and —$S(O)_2$—, preferably —NH—C(O)—;

s is an integer from 0 to 6, preferably from 1 to 4; and k is an integer from 1 to 4, preferably from 1 to 2, more preferably 1.

An example of linker B of formula (II') includes, but is not limited to:

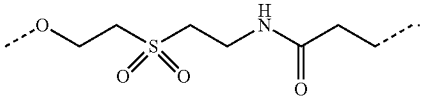

In a preferred embodiment the linker B is represented by one of the following formulae:

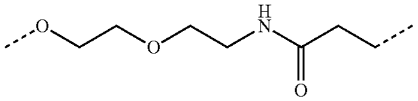

,

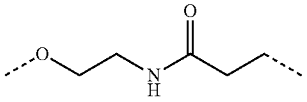

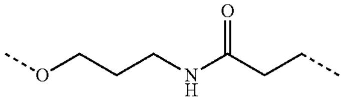

,

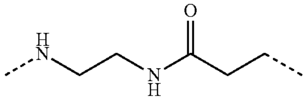

,

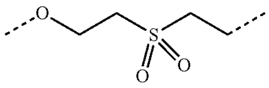

,

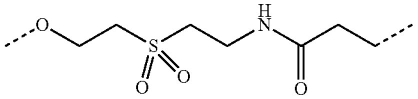

, or

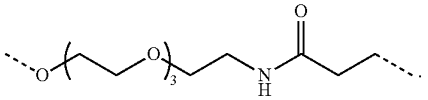

.

In a preferred embodiment, the moiety [B-$(C)_v$] is such that:

v is 1,

B is chosen from the following formulae:

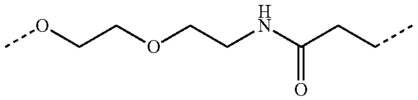

-continued

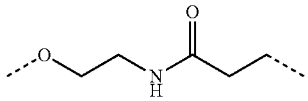

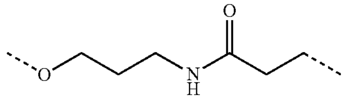

,

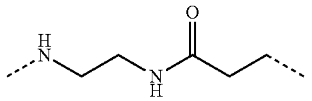

,

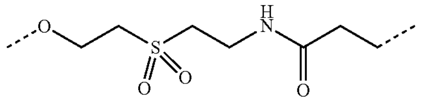

and

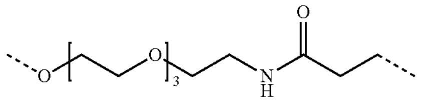

;

and

C is a functional group of formula (Mal 1) as represented above.

In another preferred embodiment, the moiety [B-$(C)_v$] is such that:

v is 1,

B is represented by the following formula:

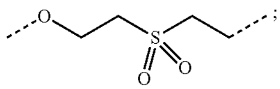

;

and

C is a functional group of formula (Mal 2) as represented above.

A compound of formula (I) according to the invention may be represented by the following formula (III):

$$A—\{[Y—(CH_2)_q—(O—CH_2—CH_2)_p—Z—(CH_2)_s]_k—(C)_v\}_w, \tag{III}$$

where A, C, v, w, Y, Z, q, p, s, and k are as defined above, including all the preferred and particular embodiments.

In a particular embodiment where the linker B is of formula (II), v is an integer from 1 to 15, preferably from 1 to 6, more preferably, v is 1 or 2, and even more preferably, v is 1. According to this more preferred embodiment, i.e. when v is 1, the functional group C is preferably at a terminal of the linker B of formula (II).

In an embodiment where v is more than 1, one functional group C is preferably at a terminal of the linker B of formula (II), and the additional functional groups C may be at any position of the linker B. Typically, each of said additional functional groups C may each replace a hydrogen atom of the linker B of formula (II).

In a particular embodiment, the moiety [B-(C)$_v$] is represented by one of the following formulae:
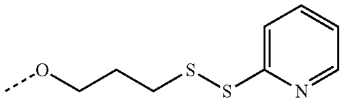,
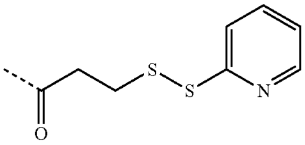,
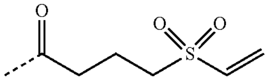,
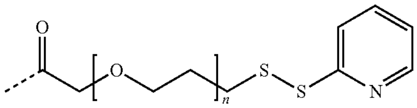,
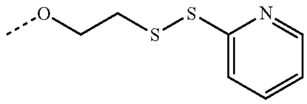,
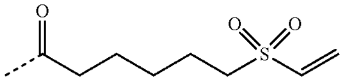,
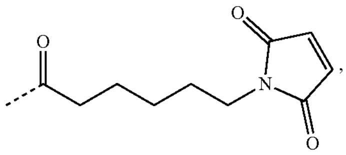,
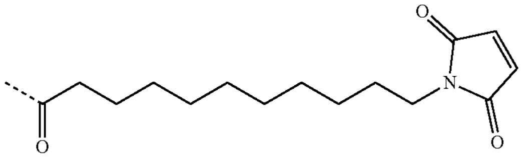,
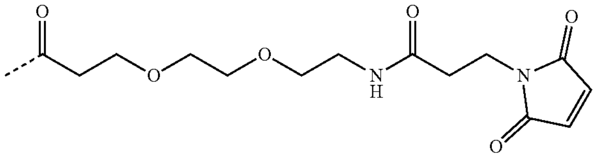,
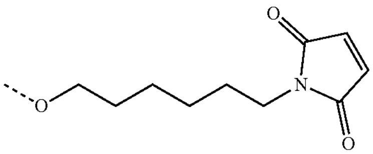,
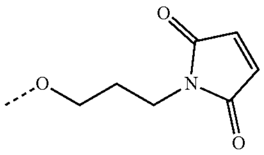,
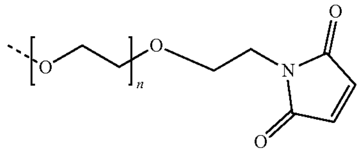,
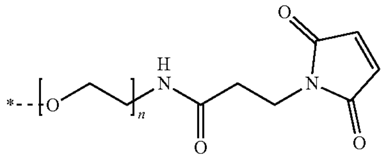,
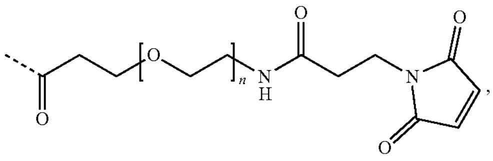,
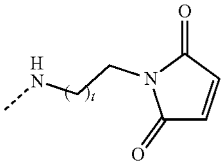,
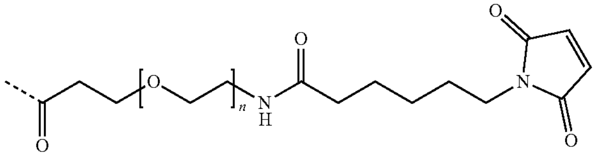,
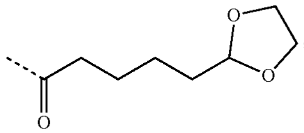,
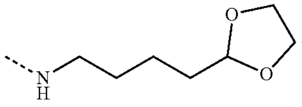,
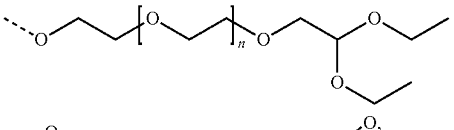,
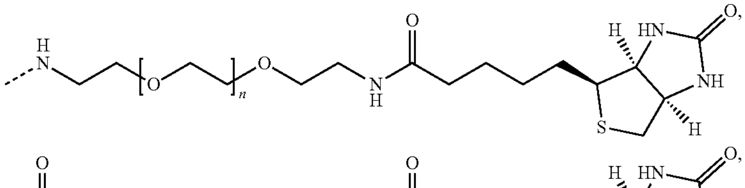,
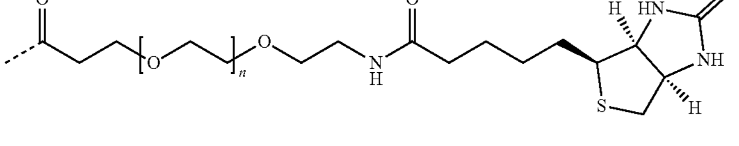

-continued
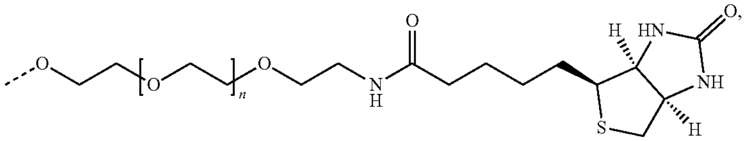
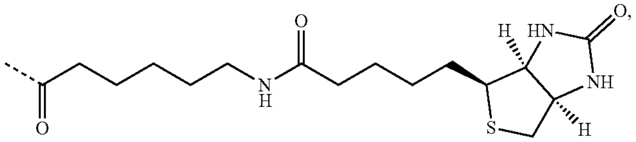
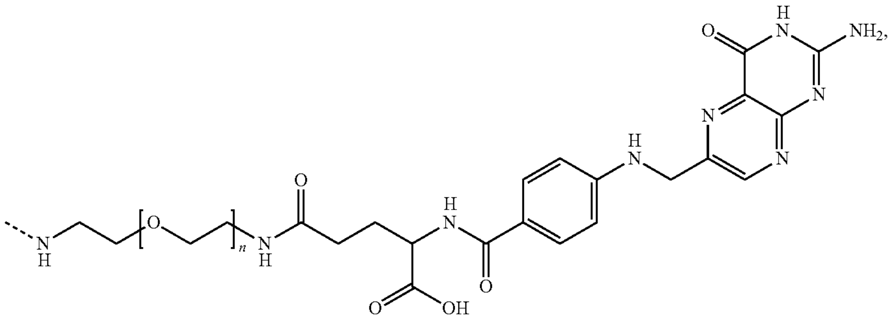
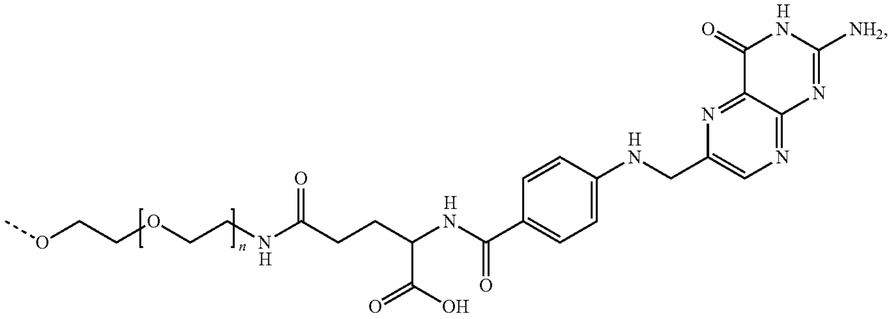
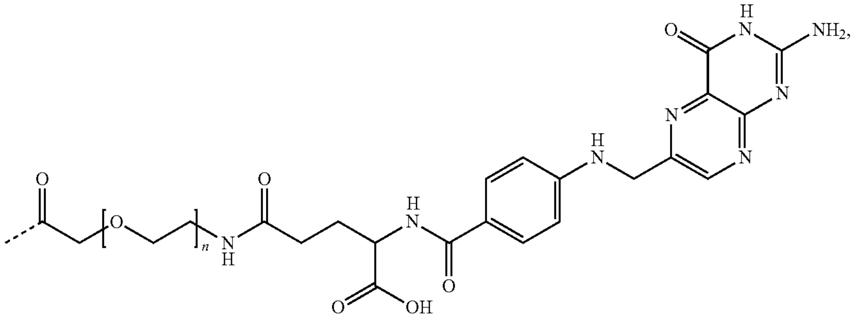
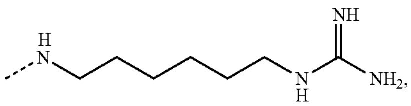
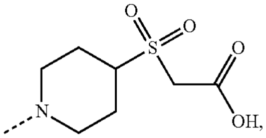
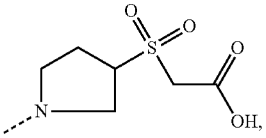
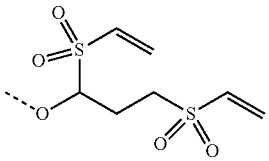
,
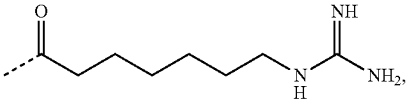
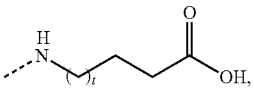
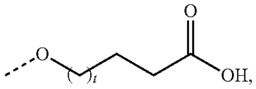
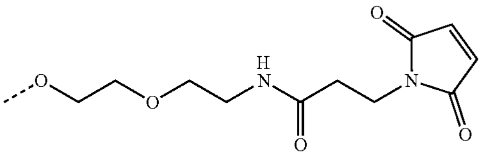
, -continued
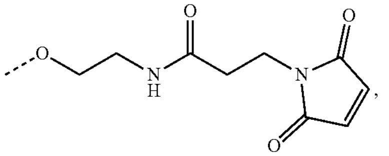
,
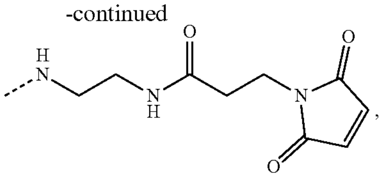
,
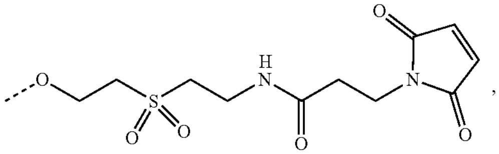
,
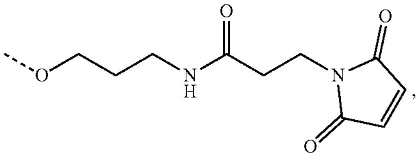
, or
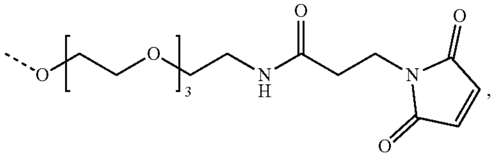
,
wherein, in each formula,
n is independently an integer from 0 to 250, preferably from 0 to 50, more preferably from 0 to 12, and
t is independently an integer from 0 to 30, preferably from 0 to 12.
Preferably, the moiety B-$(C)_v$ is represented by one of the following formulae:
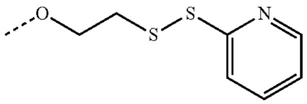
,
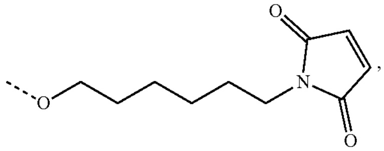
,
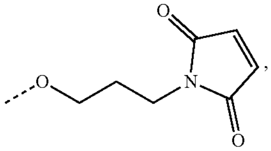
,
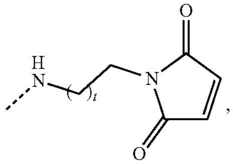
,
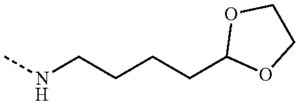
,
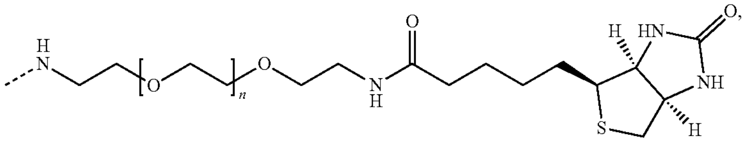
,
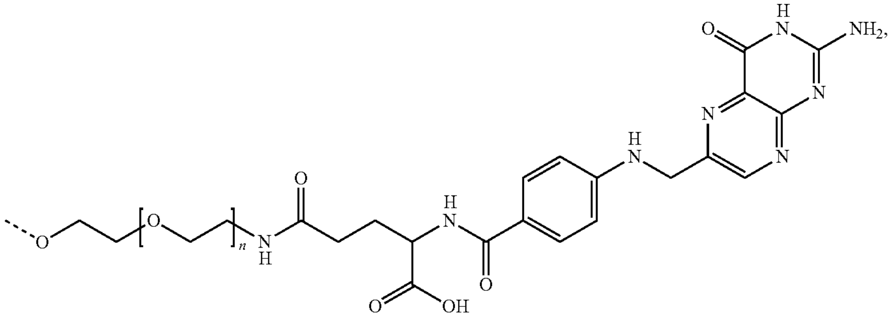
,
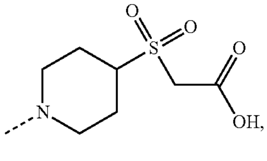
,
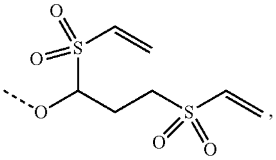
, -continued

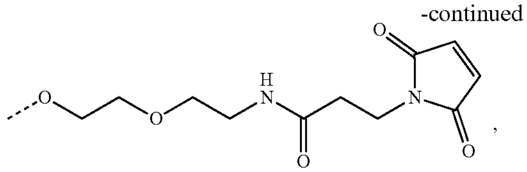
,
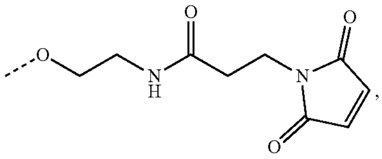
,
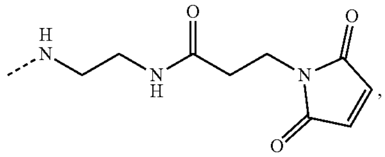
,
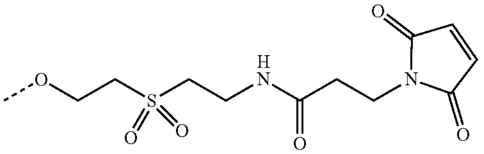
,
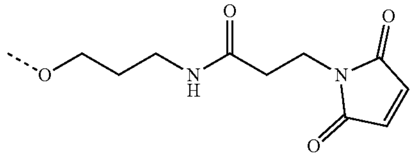
, or
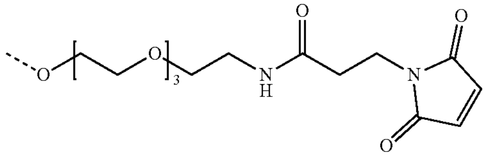

wherein, in each formula, n is independently an integer from 0 to 250, preferably from 0 to 50, more preferably from 0 to 12, and t is independently an integer from 0 to 30, preferably from 0 to 12.

More preferably, the moiety B-$(C)_v$ is represented by one of the following formulae:

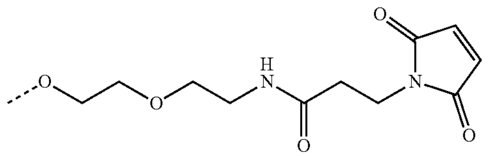
,
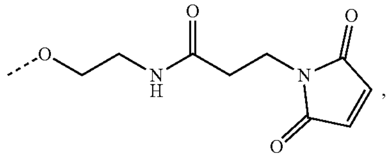
,
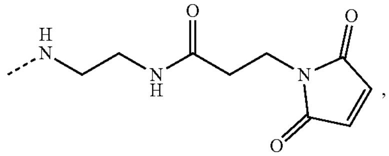
,
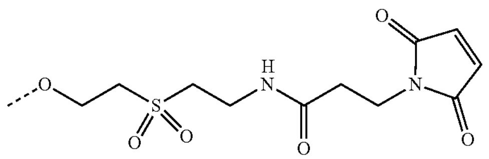
,
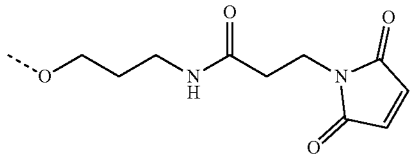
, or

-continued

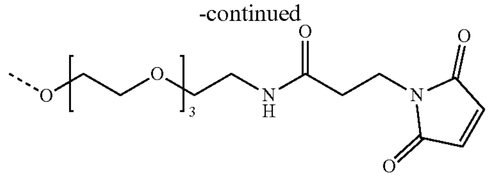
,

In a particular embodiment, the compound according to the invention is selected from the group consisting of:

2,2'-[6-(4-Methoxyphenyl)-1,3,5-triazine-2,4-diyl]bis[5-[(3-propyl-1H-pyrrole-2,5-dione) oxy]phenol];

2-[4-(diethylamino)-2-hydroxybenzoyl]-benzoic acid, 6-maleimido-1-hexanol ester;

2-[4-(diethylamino)-2-hydroxybenzoyl]benzoic acid, 2-(2-pyridinyldisulfanyl)ethanol ester;

2-[4-(diethylamino)-2-hydroxybenzoyl]benzoic acid, N-[5-(-2,5-dihydro-1H-pyrrole-2,5-dione)pentyl]amide;

2-[4-(diethylamino)-2-hydroxybenzoyl]benzoic acid, N-[4-(1,3-dioxolan-2-yl)butane] amide;

2-[4-(diethylamino)-2-hydroxybenzoyl]benzoic acid, biotine-PEG2-amide;

N-[4-(2,5-dihydro-1H-pyrrole-2,5-dione)butyl]salicylamide;

2-Cyano-3,3-diphenylpropenoic acid, 6-maleimido-1-hexanol ester;

2-Cyano-3,3-diphenylpropenoic acid, folate-PEG-1k ester;

2-Cyano-3,3-diphenylpropenoic acid, 1,3-Bis(vinylsulfonyl)-1-propanol ester;

2-Phenyl-1H-benzimidazol-5-(biotine-PEGS-N-ethyl)sulfonamide;

2-Hydroxy-4-methoxybenzophenone-5-(biotine-PEG8-N-ethyl)sulfonamide;

[N-(2-Cyano-3,3-diphenylpropenoyl)-piperidin-4-ylsulfonyl]acetic acid;

N-[(2-hydroxybenzoyl)-piperidin-4-ylsulfonyl] acetic acid;

(3-(2H-benzo[d][1,2,3]triazol-2-yl)-5(tert-butyl)-4-hydroxyphenyl)propanoic, N-[(4-piperidin-4-ylsulfonyl) acetic] amide;

2-[4-(diethylamino)-2-hydroxybenzoyl]-benzoic acid, 2-[2-[3-(2,5-dioxopyrrol-1-yl) propanoylamino]ethoxy]ethyl ester;

2-[4-(diethylamino)-2-hydroxy-benzoyl]benzoic acid, 2-[3-(2,5-dioxopyrrol-1-yl)propanoylamino]ethyl ester;

2-cyano-N-[2-[3-(2,5-dioxopyrrol-1-yl)propanoylamino]ethyl]-3,3-diphenyl-prop-2-enamide;

2-cyano-3,3-diphenyl-prop-2-enoate, 2-[2-[3-(2,5-dioxopyrrol-1-yl)propanoylamino] ethylsulfonyl]ethyl ester;

3-(2,5-dioxopyrrol-1-yl)-N-[2-[[(3Z)-3-[[4-[(Z)-[4-[2-[3-(2,5-dioxopyrrol-1-yl)propanoyl amino]ethylsulfamoylmethyl]-7,7-dimethyl-3-oxo-norbornan-2-ylidene]methyl]phenyl] methylene]-7,7-dimethyl-2-oxo-norbornan-1-yl]methylsulfonylamino] ethyl]propenamide;

3-(2,5-dioxopyrrol-1-yl)-N-[3-[4-[4-[4-[3-[3-(2,5-dioxopyrrol-1-yl)propanoylamino]propoxy]-2-hydroxy-phenyl]-6-(4-methoxyphenyl)-1,3,5-triazin-2-yl]-3-hydroxy-phenoxy]propyl]propanamide; and 3-(2,5-dioxopyrrol-1-yl)-N-[2-[2-[2-[2-[4-[4-[4-[2-[2-[2-[2-[3-(2,5-dioxopyrrol-1-yl)propanoylamino]ethoxy]ethoxy]ethoxy]ethoxy]-2-hydroxy-phenyl]-6-(4-methoxyphenyl)-1,3,5-triazin-2-yl]-3-hydroxy-phenoxy]ethoxy]ethoxy]ethoxy]ethyl]propanamide.

Preferably, the compound according to the invention is selected from the group consisting of:

2-[4-(diethylamino)-2-hydroxybenzoyl]-benzoic acid, 2-[2-[3-(2,5-dioxopyrrol-1-yl) propanoylamino]ethoxy]ethyl ester;

2-[4-(diethylamino)-2-hydroxy-benzoyl]benzoic acid, 2-[3-(2,5-dioxopyrrol-1-yl)propanoylamino]ethyl ester;

2-cyano-N-[2-[3-(2,5-dioxopyrrol-1-yl)propanoylamino]ethyl]-3,3-diphenyl-prop-2-enamide;

2-cyano-3,3-diphenyl-prop-2-enoate, 2-[2-[3-(2,5-dioxopyrrol-1-yl)propanoylamino] ethylsulfonyl]ethyl ester;

3-(2,5-dioxopyrrol-1-yl)-N-[2-[[(3Z)-3-[[4-[(Z)-[4-[2-[3-(2,5-dioxopyrrol-1-yl)propanoyl amino]ethylsulfamoylmethyl]-7,7-dimethyl-3-oxo-norbornan-2-ylidene]methyl]phenyl] methylene]-7,7-dimethyl-2-oxo-norbornan-1-yl]methylsulfonylamino] ethyl]propenamide;

3-(2,5-dioxopyrrol-1-yl)-N-[3-[4-[4-[4-[3-[3-(2,5-dioxopyrrol-1-yl)propanoylamino]propoxy]-2-hydroxy-phenyl]-6-(4-methoxyphenyl)-1,3,5-triazin-2-yl]-3-hydroxy-phenoxy]propyl]propanamide; and 3-(2,5-dioxopyrrol-1-yl)-N-[2-[2-[2-[2-[4-[4-[4-[2-[2-[2-[2-[3-(2,5-dioxopyrrol-1-yl)propanoylamino]ethoxy]ethoxy]ethoxy]ethoxy]-2-hydroxy-phenyl]-6-(4-methoxyphenyl)-1,3,5-triazin-2-yl]-3-hydroxy-phenoxy]ethoxy]ethoxy]ethoxy]ethyl]propanamide.

Properties of a Compound of Formula (I)

According to the present invention, a compound of formula (I) is adhesive. More particularly, a compound of formula (I) can be bioadhesive.

The expression "adhesive compound" denotes a compound that is able to adhere, through one or more functional groups (e.g. functional groups C as defined herein), to any support, said support being biological, organic, and/or inorganic. More specifically, said compound adheres through one or more of its functional groups (e.g. functional groups C as defined herein), which are able to react with reactive groups or entities of said support.

A "bioadhesive compound" refers to an adhesive compound as defined above, wherein the support is biological. Examples of biological supports include but are not limited to tissues (e.g. a skin), cells (e.g. chondrocytes, osteoblasts, fibroblasts, blood cells, plasmocytes), intracellular or extracellular materials (e.g. proteins, glycoproteins, collagen, elastin, glycosaminoglycans, proteoglycans).

Reactive groups that can be found on said supports, and more particularly on said biological supports, include, but are not limited to, amine, ammonium, guanidinium, thiol, carboxylic acid, and carboxylate.

Said functional groups C may advantageously react selectively with a particular reactive group found on said support. For instance:

- maleimide, thiol, Mickael acceptors, sulfonylazeridine, vinylsulfone, isocyanate, or thiocyanate can typically be selective to thiol groups;
- carboxylic acid, aldehyde, acetal, esters, NHS esters, sulfo-NHS esters, or anhydride can typically be selective to amine groups;
- carboxylate can typically be selective to ammonium;
- amine can typically be selective to carboxylic acid; and
- ammonium and guanidinium can typically be selective to carboxylate.

Reaction of a functional group C of a compound of formula (I) with a reactive group creates a bond such as amide, disulfide, thioether, thiocarbamate, imine, or ionic pair —$NH_3^+$,$^-$OOC—. The bound created between a functional group of a compound of formula (I) and a reactive group of a support may be covalent or ionic. Said bound is advantageously reversible. Said bound may be cleaved by use of a cleaving material selected from chemical and physical agents (e.g. protein, peptide (e.g. glutathione), amino acid, enzyme (e.g. cathepsin B), thiol (e.g. 2-mercaptoethanol, N-acetyl cysteine), dithiol (e.g. dithiothreitol), pH-modifier, acid, base, solvent, and/or woven or non-woven tissue. The skilled artisan is able to select an appropriate cleaving material depending on the nature of the bound and/or the composition.

In a particular embodiment, a compound of formula (I) is biocompatible.

The term "biocompatible compound" refers to a compound that is, along with any metabolites or degradation products thereof, generally non-toxic to the recipient, and do not cause any significant adverse effects to the recipient. Generally speaking, biocompatible materials (or compounds are compounds which do not elicit a significant inflammatory or immune response when administered to a patient.

In another particular embodiment, a compound of formula (I) is biodegradable.

Composition

Another object of the invention is a composition comprising at least one compound of formula (I) as defined herein and at least one excipient.

In a particular embodiment, the composition comprises from 0.01 wt % to 99 wt % of compound of formula (I), preferably from 0.01 wt % to 90 wt %, more preferably from 1 wt % to 70 wt %, even more preferably from 5 wt % to 50 wt %, relative to the total weight of the composition.

The composition according to the invention may in particular be in the form of a suspension, a cream, a spray, an aerosol, a butter, a stick, a gel, an ointment, a lotion, a solution, a solid, an emulsion, a micro-emulsion, an oil, a lyophilizate, a milk, a powder, a paste, a wax, a mousse, a patch, a film, a micelle, a liposome, or a foam. The composition can be prepared according to processes known to the skilled artisan.

The composition of the invention may comprise a solvent or a dispersion medium comprising, for instance, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

Examples of excipients include, but are not limited to, surfactants, dispersants, emulsifiers, pH modifying agents, pH-buffers, viscosity modifying agents, preservatives, polymerizers, pigments, colorants, stabilizing agents, glidants, diluents, binders, water-soluble polymers, lubricants, disintegrators, swelling agents, fillers, stabilizers, antioxidants, emulsifiers, emollients, penetration enhancers, propellants, gas, depigmenting agents, film forming agents, gelling agents, moisturizing agents, colorants, fragrance ingredients, exfoliants, solubilizers, solvents, binding agents, bulking agents, humectants, cleansing agents, elastomers, astringents, masking agents, anti-static agents, protectants, denaturants, absorbents, anti-caking agents, matting agents, structuring agents, oxidative agents, reducing agents, superfatting agents, active boosters, and combinations thereof.

Examples of additional agents which may be comprised in the composition include, but are not limited to, desquaming agents, whitening agents, tensing effect agents soothing agents, anti-irritant agents, sebo-regulating agents, wound healing agents, anti-inflammatory agents, anti-acne agents, anti-glycation agents, slimming agents, self-tanning agents, anti-aging agents, anti-wrinkle agents, Surfactants that can be used in the composition may be anionic, cationic, amphoteric or nonionic. Examples of anionic surfactants include, but are not limited to, carboxylate, sulfonate and sulfate ions-containing surfactants, such as sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; sulfated castor oil, propylene glycol, lecithin, capric/caprylic triglycerides, PEG-12 oleate (FANCOL® HS3 US®), and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, polyoxyethylene hydrogenated tallow amide, but also emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone, cetyl palmitate. Examples of amphoteric surfactants include sodium N-dodecyl-.beta.-alanine, sodium N-lauryl-.beta.-iminodipropionate, myristoamphoacetate, lauryl betaine and lauryl sulfobetaine.

Examples of preservatives, include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, perillic acid and thimerosal.

Examples of water-soluble polymers include, but are not limited to, polyvinylpyrrolidone, dextran, carboxymethylcellulose, and polyethylene glycol.

Suitable stabilizers include, but are not limited to, butylated hydroxytoluene (BHT), ascorbic acid, its salts and esters, Vitamin E, tocopherol and its salts, sulfites such as sodium metabisulphite, cysteine and its derivatives, citric acid, propyl gallate, and butylated hydroxyanisole (BHA).

An example of pH-buffer that can be used in the composition is triethanolamine.

Examples of emollients include, but are not limited to, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof.

Examples of emulsifiers include, but are not limited to, acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum, PEG-100 Stearate/Glyceryl stearate (Arlacel 165®), decyglucoside (Plantaren 2000®), laurylglucoside (Plantaren1200®), Cetearyl Glucoside, Cetearyl Alcohol (Emulgade PL68/50®), and combinations thereof.

Examples of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Examples of propellant agents include, but are not limited to, dichlorofluoromethane, difluoroethane, isobutane, n-butane, propane, dichlorofluoromethane, nitrogen, carbon dioxide.

Examples of desquaming agents include, but are not limited to, beta hydroxyacids, alpha hydroxy acids, urea, cinnamic acid, *Saphora japonica* extract, proteases like trypsine.

Examples of depigmenting agents include, but are not limited to, vitamin C and its derivatives, ferulic acid, resorcinol, alpha and beta arbutin.

Examples of anti-glycation agents include, but are not limited to, black tea extract and *Vaccinium myrtillus* extract.

Examples of slimming agents include, but are not limited to, caffeine, tea extracts, *Hedera helix* extracts, and theobromine.

Examples of soothing agents and anti-irritation agents include, but are not limited to, caffeine, vitamins E, C, B5, B3, glycyrrhetic acid, a salt or a derivative thereof.

Examples of sebo-regulating agents include, but are not limited to, zinc salts such as zinc gluconate or zinc pidolate, vitamin B6, selenium chloride, and benzoyl peroxide.

Examples of wound healing agents include, but are not limited to, arginine, hydroxyproline, chitosan and derivatives, propolis extracts, folic acid, and chitosan.

An example of self-tanning agent includes, but is not limited to, erythrulose.

Examples of anti-aging agents include, but are not limited to, placenta extracts, beta glucan, fucoidan, sodium hyaluronate, and collagen.

Examples of anti-static agents includes, but is not limited to, methyl sulfonyl methane.

An example of bulking agent includes, but is not limited to, polypropylene A.

Examples of film former include, but are not limited to, copolymer of 1-vinyl-2-pyrrolidone and vinyl acetate, and Polyquaternium-6.

Applications

The composition of the invention can be administered orally, topically, parenterally, sub-cutaneously, epicutaneously, intra-dermically, transdermically, intramusculary, enterally, intranasally, intra-respiratory, intra-vascular, ophthalmic preparation, intra-vaginal, endo-urethral, or by nasal inhalation. In a particular embodiment, the composition of the invention is administered sub-cutaneously, epicutaneously, intra-dermically, transdermically, or topically, preferably topically. The composition of the invention may be administered by microneedles, or patches.

The composition may in particular be applied to mucosa, corneum, epidermis, dermis, epithelium, endothelium, skin, skin appendages, connective tissues, or bone tissues, preferably skin, skin appendages or mucosa.

In an embodiment, the composition of the invention is selected from a sunscreen composition, a cosmetic composition, a dermatological composition, and a therapeutic composition. In a preferred embodiment, the composition is a sunscreen or a cosmetic composition.

Topical Composition

In a particular embodiment, the composition of the invention is a topical composition. The topical composition comprises at least one compound of formula (I) as defined herein, and at least one topically acceptable excipient.

A "topically acceptable excipient", as used herein, denotes an excipient suitable for a topical application. Such an excipient can be judiciously chosen by the skilled artisan, for instance among the excipients described above.

Said topical composition may be a dermatological composition, therapeutic composition and/or a cosmetic composition.

The topical composition may in particular be in the form of a suspension, a cream, a spray, an aerosol, a butter, a stick, a gel, an ointment, a lotion, a solution, a solid, an emulsion, a micro-emulsion, an oil, a lyophilizate, a milk, a powder, a paste, a wax, a mousse, a patch, a film, a micelle, a liposome, or a foam. The composition can be prepared according to processes known to the skilled artisan.

Preferably, the topical composition is selected from a cream, a spray, a gel, an ointment, a lotion, an emulsion, a foam, a suspension and a milk.

The topical composition may be applied to mucosa, corneum, epidermis, dermis, epithelium, endothelium, skin or skin appendages (e.g. hair and nails), preferably mucosa, skin or skin appendages.

Cosmetic Composition

In another particular embodiment, the composition of the invention is a cosmetic composition.

Said cosmetic composition comprises at least one compound of formula (I) according to the invention, and at least one cosmetically acceptable excipient.

A "cosmetically acceptable excipient", as used herein, denotes an excipient suitable for a cosmetic application. Such an excipient can be judiciously chosen by the skilled artisan, for instance among the excipients described above.

The cosmetic composition can be administered orally, topically, parenterally, sub-cutaneously, epicutaneously, intra-dermically, transdermically, intramusculary, enterally, intranasally, intra-respiratory, or by nasal inhalation. In a preferred embodiment, the cosmetic composition is administered topically.

Preferably, the cosmetic composition is a topical composition or a dermatological composition, more preferably a topical composition.

The cosmetic composition may in particular be applied to mucosa, corneum, epidermis, dermis, epithelium, endothelium, skin or skin appendages (e.g. hair and nails), preferably mucosa, skin or skin appendages.

The cosmetic composition may in particular be in the form of a suspension, a cream, a spray, an aerosol, a butter, a stick, a gel, an ointment, a lotion, a solution, a solid, an emulsion, a micro-emulsion, an oil, a lyophilizate, a milk, a powder, a paste, a wax, a mousse, a patch, a film, a micelle, a liposome, or a foam. The composition can be prepared according to processes known to the skilled artisan.

The composition of the invention may be particularly well-suited for combatting and/or reducing the signs of cutaneous ageing, such as the formation of wrinkles and/or fine lines, skin sagging, loss of firmness, loss of radiance and/or evenness of the complexion, and/or for reinforcing the skin barrier.

The signs of cutaneous ageing may be related to intrinsic factors that are age-related, but also extrinsic factors, in particular UV-light exposure.

An object of the invention relates to a cosmetic use of the composition of the invention for combatting and/or reducing the signs of cutaneous ageing, such as the formation of wrinkles and/or fine lines, skin sagging, loss of firmness, loss of radiance and/or evenness of the complexion, and/or for reinforcing the skin barrier.

Another object of the invention is cosmetic process for combatting and/or reducing the signs of cutaneous ageing, such as the formation of wrinkles and/or fine lines, skin sagging, loss of skin firmness, loss of radiance and/or evenness of the complexion, and/or for reinforcing the skin barrier, comprising applying topically to the skin or its appendages, a composition of the invention.

Sunscreen

In another particular embodiment, the composition of the invention is a sunscreen composition.

The sunscreen composition is advantageously applied topically (i.e. a topical composition). The sunscreen composition may in particular be in the form of a suspension, a cream, a spray, an aerosol, a butter, a stick, a gel, an ointment, a lotion, a solution, a solid, an emulsion, a micro-emulsion, an oil, a lyophilizate, a milk, a powder, a paste, a wax, a mousse, a patch, a film, a micelle, a liposome, or a foam. In a particular embodiment, the sunscreen composition is a formulation sunscreen type butter.

Therapeutic Composition

In a particular embodiment, the composition of the invention is a therapeutic composition and, more particularly, said composition is a pharmaceutical composition or veterinary composition.

The therapeutic composition comprises at least one compound of formula (I) according to the invention and at least one pharmaceutically acceptable excipient.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable excipient", as used herein, refers to all components of a pharmaceutical or therapeutic composition which facilitate the manufacture, the preservation and/or the delivery of the composition in vivo. Pharmaceutically acceptable excipients include, but are not limited to, diluents, preservatives, binders, lubricants, disintegrators, swelling agents, fillers, stabilizers, and combinations thereof.

The therapeutic composition can be administered orally, topically, parenterally, sub-cutaneously, epicutaneously, intra-dermically, transdermically, intramusculary, enterally, intranasally, intra-respiratory, or by nasal inhalation. In a preferred embodiment, the therapeutic composition is administered topically.

In a particular embodiment, the therapeutic composition is applied to a tissue chosen from the skin, skin appendages, mucosa, corneum, epidermis, dermis, epithelium, endothelium, connective tissues, bone tissues, and combinations thereof, preferably skin, skin appendages, mucosa, corneum, epidermis, dermis, epithelium, and endothelium, and more preferably skin, skin appendages, and mucosa. In another embodiment, the therapeutic composition is applied to a circulating medium, such as blood or plasma.

In a particular embodiment, the therapeutic composition is a dermatological composition.

Another object of the invention is a compound of formula (I) according to the invention or a composition of the invention (in particular, a therapeutic composition), for use in the treatment and/or prevention of a skin, a mucosa, an eye cornea, or skin appendage disease or condition. Preferably, said skin, mucosa, eye cornea or skin appendage disease or condition is chosen from lipodystrophy, keloid scars, acne, psoriasis, atopic dermatitis, actinic keratosis, rosacea, melasma, melanoma, Merker cell carcinoma, basal cell carcinoma, squamous cell carcinoma, scar treatments, wound healing, alopecia, vitiligo, urticaria (hives), cold sores, impetigo, eczema, rashes dermatitis, ichthyosis, warts, blisters, pruritus, gangrene, bruises, pustules, bacterial skin infections like leprosy, carbuncles, cellulitis, impetigo, fungal infections like Athlete's foot (intertrigo) and sporotrichosis, fungal nail infections, viral infection like herpes, sunburns, lice, scabies, pressure ulcer disinfection, pressure ulcer healing, vaginitis, bladder cancer, endometriosis, uveitis, cornea diseases, cornea keratitis, corneal herpes, keratoconus, corneal dystrophies, pharyngitis, cutaneous and mucosal allergies. More preferably, said skin, mucosa, eye cornea or skin appendage disease or condition is chosen from lipodystrophy, keloid scars, acne, psoriasis, atopic dermatitis, actinic keratosis, rosacea, melasma, melanoma, Merker cell carcinoma, basal cell carcinoma, squamous cell carcinoma, scar treatments, wound healing, alopecia, vitiligo, urticaria (hives), cold sores, impetigo, eczema, rashes dermatitis, ichthyosis, warts, blisters, pruritus, gangrene, bruises, pustules, bacterial skin infections like leprosy, carbuncles, cellulitis, impetigo, fungal infections like Athlete's foot (intertrigo) and sporotrichosis, fungal nail infections, viral infection like herpes, sunburns, lice, scabies, pressure ulcer disinfection and pressure ulcer healing.

As used herein, the terms "prevent," "preventing," or "prevention," refer to any reduction, no matter how slight, of a subject's predisposition or risk for developing a condition, disease, disorder or symptom thereof. For purposes of prevention, the subject is any subject, and preferably is a subject that is at risk for, or is predisposed to, developing a condition, disease, disorder. The term "prevention" includes either preventing the onset of a clinically evident condition, disease, disorder altogether or preventing the onset of a pre-clinically evident condition, disease, disorder in individuals at risk. This includes prophylactic treatment of subjects at risk of developing condition, disease, disorder.

As used herein, the terms "treat", "treatment" or "treating" of a disease, disorder, or condition encompass alleviation of at least one symptom thereof, a reduction in the severity thereof, or the delay or inhibition of the progression thereof. Treatment need not mean that the disease, disorder, or condition is totally cured. A useful composition herein needs only to reduce the severity of a disease, disorder, or condition, reduce the severity of symptoms associated therewith, provide improvement to a patient or subject's quality of life, or delay or inhibit the onset of a disease, disorder, or condition.

Another object of the invention is a method for delivering at least one compound of formula (I) to a tissue of a subject in need thereof, comprising administering an effective amount of a composition of the invention. The present invention also provides a method of delivering at least one compound of formula (I) to a tissue of a subject, comprising: topically administering to a subject in need thereof a therapeutically effective amount of any presently described compositions useful in treating a disease, disorder, or condition of the tissue.

Particularly, said tissue is chosen from the skin, skin appendages, corneum, epidermis, dermis, epithelium, endothelium, connective tissues, bone tissues, and combinations thereof. Preferably, said tissue is the skin, a skin appendage, or a mucosa.

"Effective amount" or "therapeutically effective amount", as used herein, refers to an amount of drug or composition of the invention as disclosed herein effective to alleviate, delay onset of, or prevent one or more symptoms of a disease or disorder.

Another object of the invention is a method for treating or preventing a skin, a mucosa, an eye cornea or skin appendage disease or condition, comprising administering to a subject in need thereof, a composition of the invention (in particular, a therapeutic composition), said composition comprising at least one compound of formula (I) as defined herein.

A further object of the invention is a method of treating or preventing a skin, a mucosa, an eye cornea or a skin appendage disease, disorder, or condition in a subject, comprising: topically administering to a subject in need thereof a therapeutically effective amount of any presently described compositions useful in treating a skin, a mucosa, or an eye cornea disease, disorder, or condition. In a particular embodiment, the skin, mucosa, or eye cornea disease, disorder, or condition is selected from lipodystrophy, keloid scars, acne, psoriasis, atopic dermatitis, actinic keratosis, rosacea, melasma, melanoma, Merker cell carcinoma, basal cell carcinoma, squamous cell carcinoma, scar treatments, wound healing, alopecia, vitiligo, urticaria (hives), cold sores, impetigo, eczema, rashes dermatitis, ichthyosis, warts, blisters, pruritus, gangrene, bruises, pustules, bacterial skin infections like leprosy, carbuncles, cellulitis, impetigo, fungal infections like Athlete's foot (intertrigo) and sporotrichosis, fungal nail infections, viral infection like herpes, sunburns, lice, scabies, pressure ulcer disinfection and pressure ulcer healing, uveitis, cornea diseases, cornea keratitis, corneal herpes, keratoconus, corneal dystrophies, pharyngitis, cutaneous and mucosal allergies.

For the purpose of clarity, any element or feature of any method or composition or process described herein, can be combined with any other element or feature of any other method or composition or process described herein.

Another object of the invention is a use of a compound of formula (I) of the invention for making a composition for treating and/or preventing a skin, mucosa, eye cornea, skin appendage disease or condition.

Another object of the invention is a compound of formula (I) of the invention or a composition of the invention (in particular, a therapeutic composition), for use in the treatment and/or prevention of a disease or condition selected in the group consisting of lipodystrophy, keloid scars, acne, psoriasis, atopic dermatitis, actinic keratosis, rosacea, melasma, melanoma, Merker cell carcinoma, basal cell carcinoma, squamous cell carcinoma, scar treatments, wound healing, alopecia, vitiligo, urticaria (hives), cold sores, impetigo, eczema, rashes dermatitis, ichthyosis, warts, blisters, pruritus, gangrene, bruises, pustules, bacterial skin infections like leprosy, carbuncles, cellulitis, impetigo, fungal infections like Athlete's foot (intertrigo) and sporotrichosis, fungal nail infections, viral infection like herpes, sunburns, lice, scabies, pressure ulcer disinfection and pressure ulcer healing, vaginitis, cancer such as bladder cancer, endometriosis, uveitis, cornea diseases, cornea keratitis, corneal herpes, keratoconus, corneal dystrophies, pharyngitis, cutaneous and mucosal allergies.

Kit

The present invention also relates to a kit comprising:

a composition according to the invention, a washing composition, and optionally an instruction guide.

In a preferred embodiment, the composition according to the invention in the kit is a topical composition. In a more preferred embodiment, the composition according to the invention in the kit is a cosmetic or a sunscreen composition, preferably a sunscreen composition.

A "washing composition" refers to a composition which enables the removal of part or all of a composition according to the invention, previously applied to a tissue such as the skin, skin appendages or a mucosa of a subject. More specifically, the washing composition enables the removal of adhesive compounds.

The washing composition may comprise at least one "washing agent" and, optionally one or more excipients. The "washing agent" refers to a chemical or biological agent which is able to break the bond between adhesive compounds adhered to a tissue and said tissue. The washing agent may be a protein, a peptide (e.g. glutathione), an amino acid, an enzyme (e.g. cathepsin B), a thiol (e.g. 2-mercaptoethanol, N-acetyl cysteine), a dithiol (e.g. dithiothreitol), a pH-modifier, an acid, a base, a solvent, a saline solution (e.g. sodium chloride solution) or a combination thereof. Said washing agent can be judiciously chosen by the skilled artisan, depending on the nature of the bond between adhesive compounds adhered to a tissue and said tissue.

In a particular embodiment, said washing composition is a powder, a shampoo, a soap, a lotion, a solution, a solid, a scrubbing, a scraper, a mousse, a foam, a syndet, a gel, a shower gel, a spray, a mist, a wax, a strip, an enzyme composition, a detergent composition or a woven or non-woven fabric.

Other Applications—Photoprotection and Photoinstability

Another object of the invention is a use of at least one compound as defined herein for reducing photodegradation and/or photoinstability of a pharmaceutical active ingredient or a cosmetic.

The term "photodegradation" refers to a partial or total degradation induced by the light, in particular UV-light.

The term "photoinstability" refers to an instability induced by the light, in particular UV-light.

A "pharmaceutical active ingredient" includes, without limitation, physically, physiologically or pharmacologically active substances. A pharmaceutical active ingredient is a substance that can be used for the treatment (e.g., therapeutic agent, vaccine antigen or antigenic material), prevention (e.g., prophylactic agent, vaccine), diagnosis (e.g., diagnostic agent), cure or mitigation of disease or illness. An active agent may also be a substance which affects the structure or function of the body, or pro-drugs, which become biologically active or more active after they have been placed in a predetermined physiological environment.

A "cosmetic" is a substance used in cosmetics uses, methods and processes, such as a sunscreen, a dye, a fragrance, a deodorant, a microbiote modulator, a skin modifier, and a skin lipid modulator.

In a particular embodiment, the at least one compound used for reducing photodegradation and/or photoinstability of a pharmaceutical active ingredient or a cosmetic, is in a form of a micelle or a liposome. Said pharmaceutical active ingredient or cosmetic may, in particular, be encapsulated within the at least one compound of the invention in a form of a micelle or a liposome.

A further object of the invention is a material comprising a support and at least one compound as defined herein, said compound being adhered to said support.

The support may be made of any organic and/or inorganic matter. In a particular embodiment, the support is a natural or synthetic polymeric support, a natural or synthetic fiber support, a stone, a metal, a plastic, a rubber or a glass support.

The invention will also be described in further detail in the following examples, which are not intended to limit the scope of this invention, as defined by the attached claims.

EXAMPLES

Example 1. Preparation of Compounds of Formula (I)

Compound #1. 2,2'-[6-(4-Methoxyphenyl)-1,3,5-triazine-2,4-diyl]bis[5-[(3-propyl-1H-pyrrole-2,5-dione) oxy]phenol]

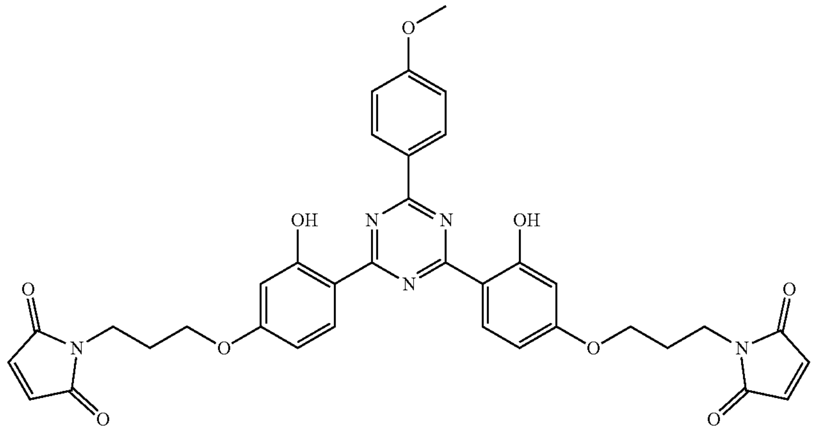 [SMILES: COc1ccc(-c2nc(-c3ccc(OCCCN4C(=O)C=CC4=O)cc3O)nc(-c3ccc(OCCCN4C(=O)C=CC4=O)cc3O)n2)cc1]

To a suspension of 2,4-bis[2,4-dihydroxyphenyl]-6-(4-methoxyphenyl)-1,3,5-triazine (200 mg, 0.49 mmol) and cesium carbonate (163 mg, 0.5 mmol) in acetonitrile (10 mL) was added 1-(3-bromopropyl)-1H-pyrrole-2,5-dione (128 mg, 0.58 mmol). The reaction mixture was refluxed overnight, filtered, and concentrated to dryness. The residue was taken in ethyl acetate, the organic phase washed with water, dried over magnesium sulfate and concentrated under vacuum. The crude residue was triturated with DIPE to obtain the desired product as white solid (250 mg).

$^1$H NMR (400 Mhz, CDCl3), δ (ppm): 2.02 (4H, t), 3.80 (4H, t, J=2.7 Hz), 3.89 (3H, s), 4.36 (4H, t, J=7.0 Hz), 6.58 (2H, dd, J=1.6 Hz), 7.03 (2H, dd, J=8.2, 1.6 Hz), 7.15 (2H, ddd, J=8.8, 1.4, 0.4 Hz), 7.45 (4H, d, J=10.2 Hz), 7.83-7.88 (4H).

Compound #2. 2-[4-(diethylamino)-2-hydroxybenzoyl]-benzoic acid, 6-maleimido-1-hexanol ester

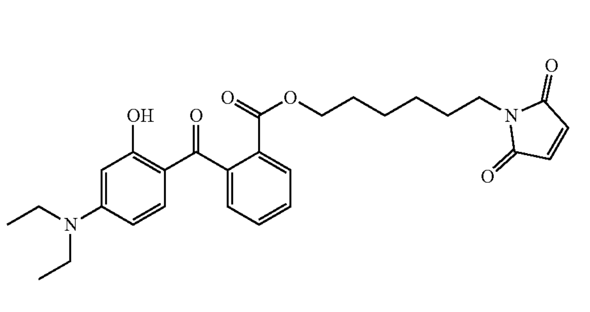 [SMILES: CCN(CC)c1ccc(C(=O)c2ccccc2C(=O)OCCCCCCN2C(=O)C=CC2=O)c(O)c1]

A solution of 156 mg (0.5 mmol) of 2-(4-diethylamino-2-hydroxybenzoyl)benzoic acid, 78 mg (0.5 mmol) of EDCI, 100 mg (0.5 mmol) of 6-maleimido-1-hexanol and 10 mg of DMAP in 30 mL of dichloromethane was stirred for 2 h at room temperature. The reaction mixture was washed with water, 1N HCl, aqueous $NaHCO_3$ and again with water, dried with Na2SO4 and the solvent was evaporated under vacuum. The crude product was filtered through a short silica column (solvent EtOAc) and 75 mg of the desired product was obtained as a light-yellow solid.

$^1$HNMR (CDCl3), δ (ppm): 1.10 (6H, t, J=7.0 Hz), 1.29-1.44 (4H), 1.64 (2H, tt, J=7.6, 7.1 Hz), 1.73 (2H, tt, J=7.4, 7.1 Hz), 3.39 (4H, q, J=7.0 Hz), 3.77 (2H, t, J=7.6 Hz), 4.19 (2H, t, J=7.1 Hz), 6.39 (1H, dd), 7.18 (1H, dd, J=7.9, 1.3 Hz), 7.45 (2H, d, J=10.2 Hz), 7.63 (1H, ddd, J=7.8, 7.7, 1.3 Hz), 7.58-7.71 (3H), 7.82 (1H, dd, J=7.9, 0.4 Hz).

Compound #3. 2-[4-(diethylamino)-2-hydroxybenzoyl]benzoic acid, 2-(2-pyridinyldisulfanyl)ethanol ester

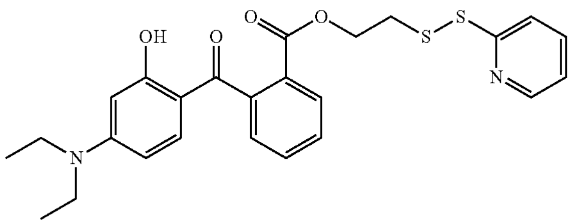 [SMILES: CCN(CC)c1ccc(C(=O)c2ccccc2C(=O)OCCSSc2ccccn2)c(O)c1]

Compound #3 was prepared using the same protocol as for compound #2 replacing the 6-maleimido-1-hexanol by the 2-(2-Pyridinyldisulfanyl)ethanol. 54 mg of the desired product were obtained as a pale yellow solid.

$^1$HNMR (CDCl3) d (ppm): 1.10 (6H, t, J=7.0 Hz), 3.39 (4H, q, J=7.0 Hz), 3.50 (2H, t, J=5.5 Hz), 4.45 (2H, t, J=5.5 Hz), 6.39 (1H, dd, J=1.3, 0.4 Hz), 7.16-7.25 (2H, dl), 7.36 (1H, ddd, J=7.8, 1.7, 0.5 Hz), 7.58-7.71 (4H), 7.79-7.88 (2H), 8.43 (1H, ddd, J=5.4, 1.9, 0.5 Hz).

Compound #4. 2-[4-(diethylamino)-2-hydroxybenzoyl]benzoic acid, N-[5-(-2,5-dihydro-1H-pyrrole-2,5-dione)pentyl]amide

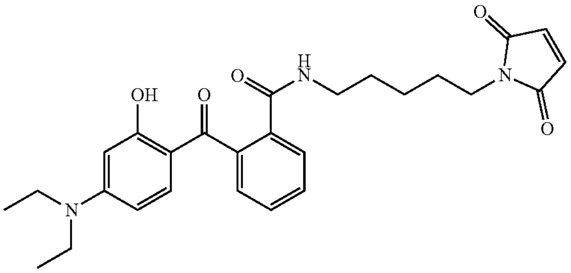 [SMILES: CCN(CC)c1ccc(C(=O)c2ccccc2C(=O)NCCCCCN2C(=O)C=CC2=O)c(O)c1]

Compound #4 was prepared using the same protocol as for compound #2 replacing the 6-maleimido-1-hexanol by the 1-(5-aminopentyl)-2,5-dihydro-1H-pyrrole-2,5-dione. 210 mg of the desired product were obtained as a white solid.

$^1$HNMR (CDCl3) d (ppm): 1.10 (6H, t, J=7.0 Hz), 1.44 (2H, tt, J=7.4, 7.1 Hz), 1.61-1.77 (4H), 3.39 (4H, q, J=7.0 Hz), 3.77 (2H, t, J=7.5 Hz), 4.20 (2H, t, J=7.1 Hz), 6.39 (1H, dd, J=1.3, 0.4 Hz), 7.18 (1H, dd, J=7.9, 1.3 Hz), 7.45 (2H, d, J=10.2 Hz), 7.58-7.71 (4H), 7.82 (1H, dd, J=7.9, 0.4 Hz).

Compound #5. 2-[4-(diethylamino)-2-hydroxybenzoyl]benzoic acid, N-[4-(1,3-dioxolan-2-yl)butane] amide

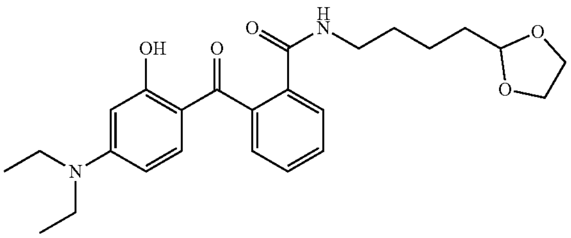 [SMILES: CCN(CC)c1ccc(C(=O)c2ccccc2C(=O)NCCCCC2OCCO2)c(O)c1]

Compound #5 was prepared using the same protocol as for compound #2 replacing the 6-maleimido-1-hexanol by the 4-(1,3-dioxolan-2-yl)butan-1-amine. 165 mg of the desired product were obtained as beige solid.

$^1$HNMR (CDCl3) d (ppm): 1.10 (6H, t, J=7.0 Hz), 1.47-1.62 (6H, dt, J=7.4, 7.3 Hz), 3.18 (2H, t, J=7.1 Hz), 3.39 (4H, q, J=7.0 Hz), 3.77-3.92 (4H, 3.84 (ddd, J=10.4, 9.2, 5.7 Hz), 4.92 (1H, t, J=5.8 Hz), 6.39 (1H, dd, J=1.3, 0.4 Hz), 7.18 (1H, dd, J=7.9, 1.3 Hz), 7.55-7.67 (4H), 7.82 (1H, dl, J=7.9 Hz).

Compound #6. 2-[4-(diethylamino)-2-hydroxybenzoyl]benzoic acid, biotine-PEG2-amide

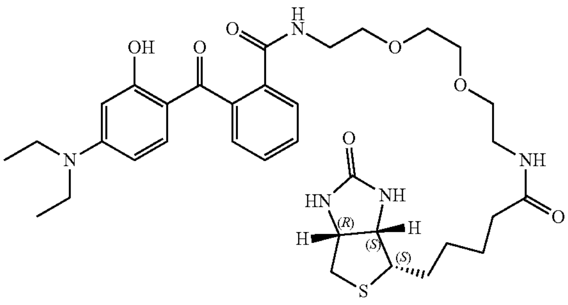

Compound #6 was prepared using the same protocol as for compound #2 replacing the 6-maleimido-1-hexanol by biotine-PEG2-amine. 257 mg of the desired product were obtained as white solid.

$^1$HNMR (DMSO $d_6$) d (ppm): 1.05-1.24 (8H), 1.41-1.62 (3H), 1.54 (1H, tt, J=7.7, 7.4 Hz), 2.13-2.21 (2H, t, J=7.4 Hz), 3.05-3.19 (2H, dd), 3.37-3.42 (4H, q), 3.43-3.51 (6H), 3.53-3.60 (2H, t, J=6.1 Hz), 3.62-3.67 (4H, t, J=4.2 Hz), 3.74 (1H, dt, J=5.8, 4.5 Hz), 3.94-4.06 (2H, dl, J=8.1, 5.8 Hz), 6.39 (1H, dd, J=1.3 Hz), 7.18 (1H, dd, J=7.9, 1.3 Hz), 7.55-7.67 (4H, dl, J=7.8), 7.82 (1H, dl, J=7.9 Hz).

Compound #7. N-[4-(-2,5-dihydro-1H-pyrrole-2,5-dione)butyl]salicylamide

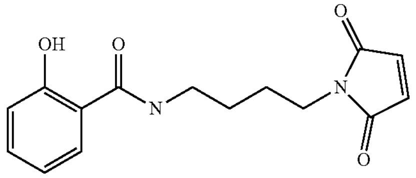 [SMILES: O=C(NCCCCN1C(=O)C=CC1=O)c1ccccc1O]

Salicyloyl chloride (156 mg, 1 mmol) was dissolved in THF (10 mL) and the 1-(4-aminobutyl)-2,5-dihydro-1H-pyrrole-2,5-dione (168 mg, 1 mmol) was added to the resultant solution. The solution was stirred for 10 minutes then triethylamine (279 µL, 2 mmol) was added slowly to the mixture. The reaction was stirred for 3 hours. TLC analysis of the reaction mixture shows a complete disappearance of the starting material. The reaction was then quenched with 40 mL of 10% hydrochloric acid solution. The solution was extracted with dichloromethane (2×30 mL). The combined organic phase was washed with a saturated sodium bicarbonate solution (2×20 mL), dried and evaporated under vacuum. The resulting residue was purified by flash column chromatography (silica gel, step gradient from 9:1 dichloromethane/MeOH to MeOH) to obtain 236 mg of product.

$^1$HNMR (CDCl3) d (ppm): 1.58 (2H, tt, J=7.9, 7.2 Hz), 1.70 (2H, tt, J=7.9, 7.6 Hz), 3.16 (2H, t, J=7.2 Hz), 3.77 (2H, t, J=7.6 Hz), 7.02 (1H, dd, J=8.3, 1.3 Hz), 7.28 (1H, ddd, J=8.1, 7.4, 1.3 Hz), 7.40-7.49 (4H).

Compound #8. 2-Cyano-3,3-diphenylpropenoic acid, 6-maleimido-1-hexanol ester

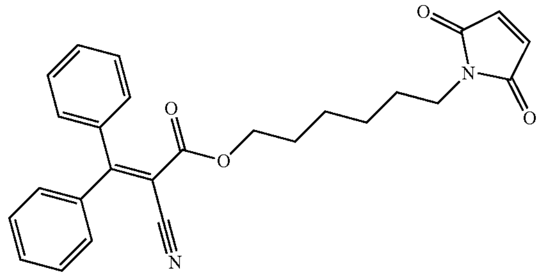 [SMILES: N#CC(C(=O)OCCCCCCN1C(=O)C=CC1=O)=C(c1ccccc1)c1ccccc1]

A solution of 125 mg (0.5 mmol) of 2-Cyano-3,3-diphenylpropenoic acid, 78 mg (0.5 mmol) of EDCI, 100 mg (0.5 mmol) of 6-Maleimido-1-hexanol and 10 mg of DMAP in 30 mL of dichloromethane was stirred for 6 h at room temperature. The reaction mixture was washed with water, dilutes HCl, aqueous $NaHCO_3$ and again with water, dried with Na2SO4 and the solvent was evaporated under vacuum. The crude product was filtered through a short silica column (solvent EtOAc) and 175 mg of the desired product was obtained as a light-yellow solid.

$^1$HNMR (CDCl3) d (ppm): 1.29-1.44 (4H, tt, J=7.1, 7.0 Hz), 1.64 (2H, tt, J=7.6, 7.1 Hz), 1.73 (2H, tt, J=7.4, 7.1 Hz), 3.77 (2H, t, J=7.6 Hz), 4.17 (2H, t, J=7.1 Hz), 7.45 (2H, d, J=10.2 Hz), 7.51-7.60 (4H), 7.70-7.79 (6H).

Compound #9. 2-Cyano-3,3-diphenylpropenoic acid, folate-PEG-1k ester

Compound #9 was prepared using the same protocol as for compound #8 replacing the 6-maleimido-1-hexanol by the folate-PEG-OH 1 kDA (nanosoft polymers) and using DMF as solvent. At the end of reaction, DMF was evaporated, the residue precipitated in a mixture of methanol/acetone, washed several time with acetone and dried under vacuum.

Compound #10. 2-Cyano-3,3-diphenylpropenoic acid, 1,3-Bis(vinylsulfonyl)-1-propanol ester

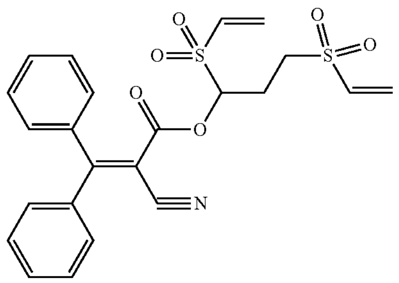

Compound #10 was prepared using the same protocol as for compound #8 replacing the 6-maleimido-1-hexanol by the 1,3-Bis(vinylsulfonyl)-1-propanol. 71 mg of the desired product were obtained as a white solid.

$^1$HNMR (CDCl3) d (ppm): 2.17-2.29 (2H, dt, J=7.5, 7.0 Hz), 3.61-3.69 (2H, t, J=7.0 Hz), 6.11 (1H, t, J=7.5 Hz), 6.92-7.01 (2H, dd, J=10.7, 1.8 Hz), 7.14-7.37 (3H, dd, J=16.9, 1.8 Hz), 7.51-7.80 (11H).

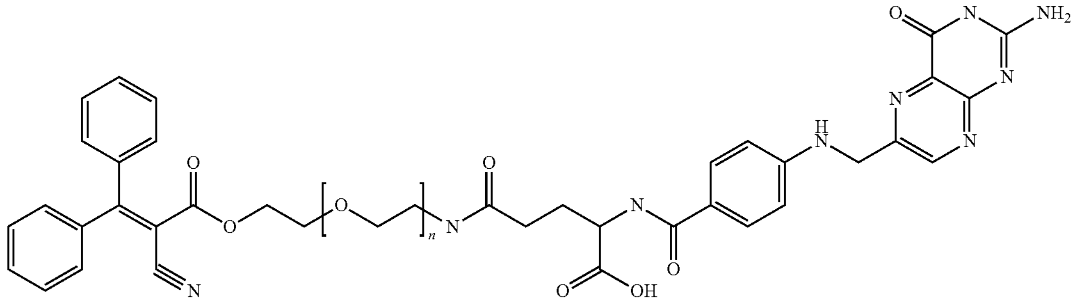

Compound #11. 2-Phenyl-1H-benzimidazol-5-(biotine-PEGS-N-ethyl)sulfonamide

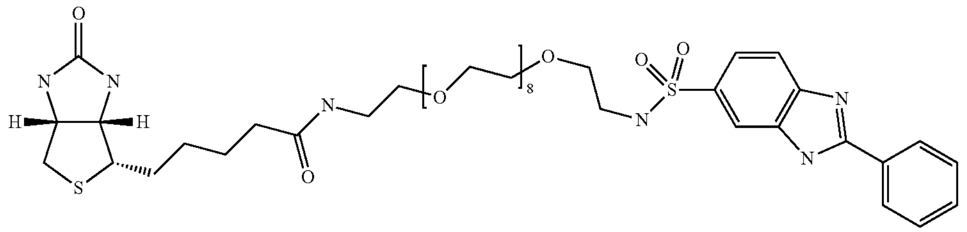

To a solution of O-(2-Aminoethyl)-O'-[2-(biotinylamino) ethyl]octaethylene glycol (285 mg, 0.41 mmol) and triethylamine (279 μL, 2 mmol) in THF (15 mL) was added 2-Phenyl-1H-benzimidazol-5-sulfonylchloride hydrochloride (164 mg, 0.5 mmol). The reaction was stirred for 4 hours and then quenched with 40 mL of 10% hydrochloric acid solution. The solution was extracted with dichloromethane (2×30 mL). The combined organic phase was washed with a saturated sodium bicarbonate solution (2×20 mL), dried and evaporated under vacuum. The resulting residue was purified by flash column chromatography (silica gel, step gradient from 9:1 dichloromethane/MeOH to MeOH) to obtain 326 mg of product.

HRMS $(M+H)^+=939$

Compound #12. 2-Hydroxy-4-methoxybenzophenone-5-(biotine-PEG8-N-ethyl)sulfonamide

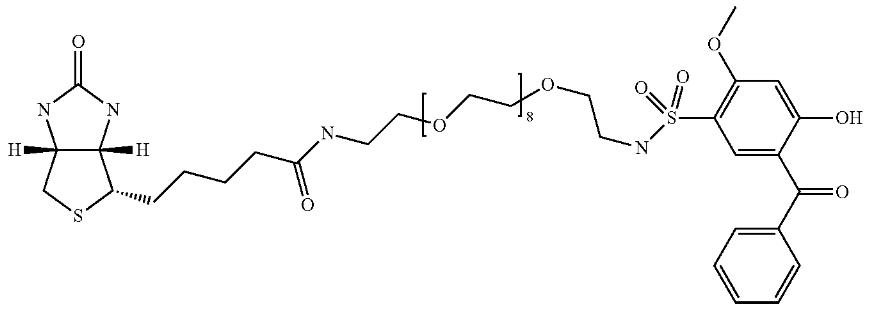

Compound #12 was prepared using the same protocol as for compound #11 replacing the 2-Phenyl-1H-benzimidazol-5-sulfonylchlorid hydrochloride by 2-hydroxy-4-methoxybenzophenone-5-sulfonyl chloride. 76 mg of the desired product were obtained as beige solid.

MRMS $(M+H)^+=973$

Compound #13. [N-(2-Cyano-3,3-diphenylpropenoyl)-piperidin-4-ylsulfonyl]acetic acid

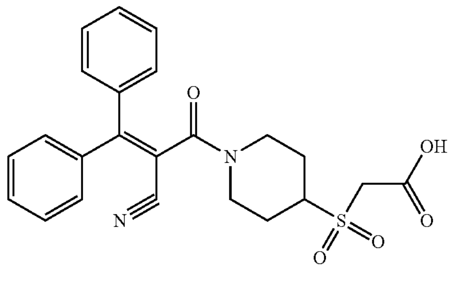 [SMILES: N#CC(C(=O)N1CCC(S(=O)(=O)CC(=O)O)CC1)=C(c1ccccc1)c1ccccc1]

A solution of 125 mg (0.5 mmol) of 2-Cyano-3,3-diphenylpropenoic acid, 78 mg (0.5 mmol) of EDCI, 110 mg (0.5 mmol) of methyl-(piperidin-4-ylsulfonyl) acetate and 10 mg of DMAP in 30 mL of dichloromethane was stirred overnight at room temperature. The reaction mixture was washed with water, dilutes HCl, aqueous $NaHCO_3$ and again with water, dried with Na2SO4 and the solvent was evaporated under vacuum. The crude product was filtered through a short silica column (solvent DCM/MeOH) and 203 mg of the desired ester was obtained as off-white solid. This later was suspended in 5 mL of THF and 1 mL of NaOH 1N was added. The reaction mixture was stirred 2 h at room temperature, acidified with HCl 0.5N and the precipitate filtered to give 180 mg of the desired product.

$^1$HNMR (DMSO d6) d (ppm): 2.14 (2H, dl), 2.60 (2H, dl), 3.23-3.40 (4H, 3.31), 3.50 (1H, tt, J=10.3, 2.7 Hz), 4.36 (2H, s), 7.50-7.59 (4H), 7.68-7.76 (6H).

Compound #14. N-[(2-hydroxybenzoyl)-piperidin-4-ylsulfonyl] acetic acid

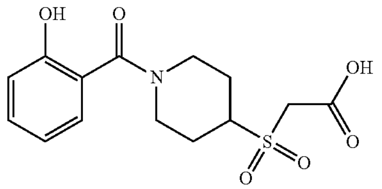 [SMILES: O=C(O)CS(=O)(=O)C1CCN(C(=O)c2ccccc2O)CC1]

A solution of 70 mg (0.5 mmol) of 2-hydroxybenzoic acid, 78 mg (0.5 mmol) of EDCI, 110 mg (0.5 mmol) of methyl-(piperidin-4-ylsulfonyl) acetate and 3 mg of DMAP in 10 mL of dichloromethane was stirred overnight at room temperature. The reaction mixture was washed with water, dilutes HCl, aqueous $NaHCO_3$ and again with water, dried with Na2SO4 and the solvent was evaporated under vacuum. The crude product was filtered through a short silica column (solvent DCM/MeOH) and 147 mg of the desired ester was obtained as off-white solid. This later was suspended in 5 mL of THF and 1 mL of NaOH 1N was added. The reaction mixture was stirred 2 h at room temperature, acidified with HCl 0.5N and the precipitate filtered to give 89 mg of the desired product.

$^1$HNMR (DMSO d6) d (ppm): 2.15 (2H, dl), 2.59 (2H, dl), 3.27-3.42 (4H), 3.49 (1H, tt, J=10.3, 2.7 Hz), 4.36 (2H, s), 7.02 (1H, dd, J=8.3, 1.3 Hz), 7.29 (1H, ddd, J=8.1, 7.4, 1.3 Hz), 7.45 (1H, ddd, J=8.3, 7.4, 1.4 Hz), 7.74 (1H, dd, J=8.1, 1.4 Hz).

Compound #15. (3-(2H-benzo[d][1,2,3]triazol-2-yl)-5(tert-butyl)-4-hydroxyphenyl)propanoic, N-[(4-piperidin-4-ylsulfonyl)acetic] amide

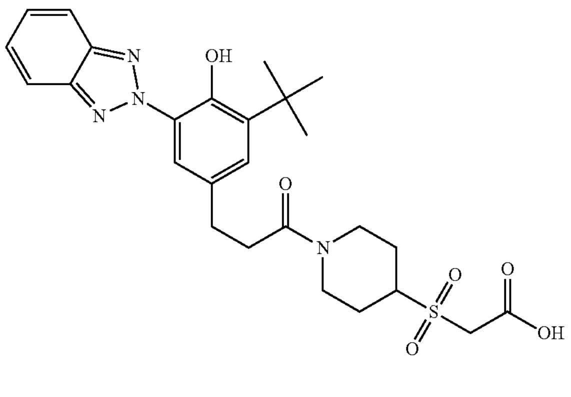 [SMILES: CC(C)(C)c1cc(CCC(=O)N2CCC(S(=O)(=O)CC(=O)O)CC2)cc(-n2nc3ccccc3n2)c1O]

A solution of 170 mg (0.5 mmol) of 3-(3-(2H-benzo[d][1,2,3]triazol-2-yl)-5(tert-butyl)-4-hydroxyphenyl)propanoic acid, 78 mg (0.5 mmol) of EDCI, 110 mg (0.5 mmol) of methyl-(piperidin-4-ylsulfonyl) acetate and 5 mg of DMAP in 15 mL of dichloromethane was stirred overnight at room temperature. The reaction mixture was washed with water, dilutes HCl, aqueous $NaHCO_3$ and again with water, dried with Na2SO4 and the solvent was evaporated under vacuum. The crude product was filtered through a short silica column (solvent DCM/MeOH) and 98 mg of the desired ester was obtained as off-white solid. This later was suspended in 5 mL of THF and 1 mL of NaOH 1N was added. The reaction mixture was stirred 2 h at room temperature, acidified with HCl 0.5N and the precipitate filtered to give 75 mg of the desired product.

$^1$HNMR (DMSO d6) d (ppm): 1.26 (9H, s), 2.16 (2H, dl), 2.54-2.65 (4H), 2.95 (2H, t, J=7.0 Hz), 3.27-3.42 (4H), 3.49 (1H, tt, J=10.3, 2.7 Hz), 4.36 (2H, s), 6.96 (1H, d, J=1.6 Hz), 7.64 (1H, d, J=1.6 Hz), 7.72 (2H, ddd, J=8.0, 7.3, 1.9 Hz), 8.25 (2H, ddd, J=8.0, 1.9, 0.5 Hz).

Compound #16. 2-[4-(diethylamino)-2-hydroxybenzoyl]-benzoic acid, 2-[2-[3-(2,5-dioxopyrrol-1-yl) propanoylamino]ethoxy]ethyl ester

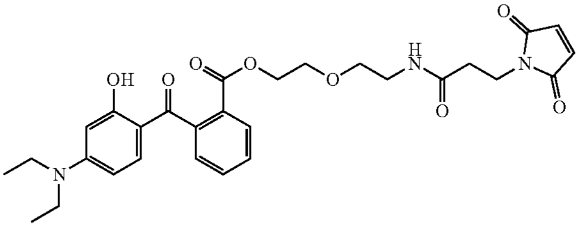 [SMILES: CCN(CC)c1ccc(C(=O)c2ccccc2C(=O)OCCOCCNC(=O)CCN2C(=O)C=CC2=O)c(O)c1]

a) 3-(diethylamino)benzo[c][1]benzoxepine-6,11-dione

In a 50 mL pear flask equipped with magnetic stirring, to a suspension of 2-[4-(diethylamino)-2-hydroxy-benzoyl] benzoic acid (4.90 g; 15.64 mmol) in 20 ml of ethyl acetate, was added a solution of DCC (3.48 g; 16.89 mmol) in 10 ml of ethyl acetate. The mixture was stirred at RT for 18 h. Then 30 ml of petroleum ether were added. After stirring for 0.5 h, the solid was filtered and washed with AcOEt/Petroleum ether to give 3.97 g of 3-(diethylamino)benzo[c][1]benzoxepine-6,11-dione as a yellow solid (yield=86%).

LCMS-ESI: $[M+H]^+$=296 b) 2-[3-(2,5-dioxopyrrol-1-yl)-N-[2-(2-hydroxyethoxy)ethyl]propanamide

In a 100 mL round bottom flask equipped with magnetic stirring, 2-(2-Aminoethoxy)ethanol (1.185 g; 11.27 mmol) was charged in DCM (100 mL). At +5° C. 3-(Maleimido) propionic acid N-hydroxysuccinimide ester (3.00 g; 11.27 mmol) was slowly added. The reaction was stirred at room temperature ("RT") for 4 h. DCM was evaporated under reduce pressure to give 4.25 g of 2-[3-(2,5-dioxopyrrol-1-yl)-N-[2-(2-hydroxyethoxy)ethyl]propanamide as a colorless oil (yield=quantitative). The product was directly used in the next step without purification. LCMS-ESI: $[M+H]^+$ =257 c) 2-[4-(diethylamino)-2-hydroxybenzoyl]-benzoic acid, 2-[2-[3-(2,5-dioxopyrrol-1-yl) propanoylamino]ethoxy]ethyl ester In a 250 mL round bottom flask equipped with magnetic stirring, 3-(diethylamino)benzo[c][1]benzoxepine-6,11-dione (3.10 g; 10.50 mmol) and 2-[3-(2,5-dioxopyrrol-1-yl)-N-[2-(2-hydroxyethoxy)ethyl]propanamide (3.90 g; 10.50 mmol) were charged in 50 mL of diglyme. DBU (1,8-Diazabicyclo[5.4.0]undec-7-ene) (0.16 g; 1.05 mmol) was added and the reaction was stirred at RT for 4 days. Diglyme was evaporated under reduced pressure and the crude oil was directly purified on 40 g $SiO_2$ column, eluted with a gradient of cyclohexane-acetone from 95/5 to 50/50 to give 1.40 g of 2-[4-(diethylamino)-2-hydroxybenzoyl]-benzoic acid, 2-[2-[3-(2,5-dioxopyrrol-1-yl) propanoylamino] ethoxy]ethyl ester as a yellow oil (yield=24%).

LCMS-ESI: $[M+H]^+$=552

$^1$H NMR 400 MHz, $DMSOd_6$, δ (ppm): 1.10 (6H, t, J=7.0 Hz), 2.31 (2H, t, J=1 Hz), 3.10 (2H, t), 3.29-3.31 (2H, m), 3.37 (4H, q, J=7.0 Hz), 3.41 (2H, sl), 3.58 (2H, t, J=7 Hz), 4.21 (2H, t, J=7.4 Hz), 6.10 (1H, sl), 6.20 (1H, dd, J=8 Hz), 6.82 (1H, d, J=8 Hz), 7.0 (2H, s), 7.45 (1H, d, J=8 Hz), 7.66 (2H, td), 8.0 (2H, d, J=8 Hz), 12.54 (1H, sl).

$\tilde{\lambda}_{max}$ UV absorbance of diethylamino hydroxybenzoyl hexyl benzoate in ethanol/DMSO 9/1 was measured at 357 nm and $\tilde{\lambda}_{max}$ UV absorbance of Compound #16 was measured at 357 nm.

Compound #17. 2-[4-(diethylamino)-2-hydroxy-benzoyl]benzoic acid, 2-[3-(2,5-dioxopyrrol-1-yl) propanoylamino]ethyl ester

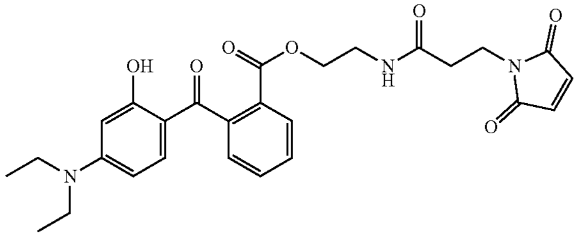 [SMILES: CCN(CC)c1ccc(C(=O)c2ccccc2C(=O)OCCNC(=O)CCN2C(=O)C=CC2=O)c(O)c1]

a) 3-(2,5-dioxopyrrol-1-yl)-N-(2-hydroxyethyl)propanamide

In a 250 mL round bottom flask equipped with magnetic stirring, 2-aminoethanol (0.838 g, 13.72 mmol) was charged in DCM (100 mL). At +5° C. 3-(maleimido)propionic acid N-hydroxysuccinimide ester (3.32 g; 12.47 mmol) was slowly added. The reaction was stirred at RT for 2 h. DCM was evaporated under reduce pressure to give 4.15 g of 3-(2,5-dioxopyrrol-1-yl)-N-(2-hydroxyethyl)propanamide as a white solid. The product was directly used in the next step without purification.

LCMS-ESI: $[M+H]^+$=213 b) 2-[4-(diethylamino)-2-hydroxy-benzoyl]benzoic acid, 2-[3-(2,5-dioxopyrrol-1-yl)propanoylamino] ethyl ester In a 250 mL round bottom flask equipped with magnetic stirring, 3-(diethylamino)benzo[c][1]benzoxepine-6,11-dione (3.68 g; 12.47 mmol) and 3-(2,5-dioxopyrrol-1-yl)-N-(2-hydroxyethyl)propanamide (4.08 g; 12.47 mmol) were charged in 50 mL of diglyme. DBU (1,8-Diazabicyclo[5.4.0]undec-7-ene) (0.16 g; 1.05 mmol) was added and the reaction was stirred at RT for 4 days. Diglyme was evaporated under reduce pressure and the crude oil was directly purified on 40 g $SiO_2$ column, gradient cyclohexane-acetone from 95/5 to 50/50 to give 1.40 g of 2-[4-(diethylamino)-2-hydroxy-benzoyl]benzoic acid, 2-[3-(2,5-dioxopyrrol-1-yl) propanoylamino]ethyl ester as a yellow solid (yield=22%).

LCMS-ESI: $[M+H]^+$=508

$^1$H NMR 400 MHz, $DMSOd_6$, δ (ppm): 1.10 (6H, t, J=7.0 Hz), 2.32 (2H, t, J=6.4 Hz), 3.24 (2H, dl), 3.37 (4H, q, J=7.0 Hz), 3.59 (2H, t, J=6.4 Hz), 4.06 (2H, t, J=7.4 Hz), 6.09 (1H, s), 6.18 (1H, dd, J=8 Hz), 6.80 (1H, d, J=8 Hz), 6.97 (2H, s), 7.43 (1H, d, J=8 Hz), 7.69 (2H, td), 8.04 (2H, d, J=8 Hz), 12.51 (1H, sl).

$\tilde{\lambda}_{max}$ UV absorbance of diethylamino hydroxybenzoyl hexyl benzoate in ethanol/DMSO 9/1 was measured at 357 nm and $\tilde{\lambda}_{max}$ UV absorbance of Compound #17 was measured at 357 nm.

Compound #18. 2-cyano-N-[2-[3-(2,5-dioxopyrrol-1-yl)propanoylamino]ethyl]-3,3-diphenyl-prop-2-enamide

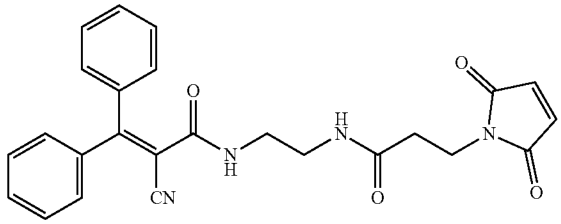 [SMILES: N#CC(C(=O)NCCNC(=O)CCN1C(=O)C=CC1=O)=C(c1ccccc1)c1ccccc1]

a) 2-cyano-3,3-diphenyl-prop-2-enoic acid

In a 250 mL round bottom flask equipped with magnetic stirring, octocrylene (10.48 g, 28.99 mmol) was solubilized in THF (75 mL). Then a solution of sodium hydroxide 1N (31.89 mL, 31.89 mmol) was added at 5° C. The reaction mixture was stirred at RT for 18 h, then acidified with HCl 1N (31.89 mL, 31.89 mmol). THF was evaporated under reduced pressure, the crude product stirred with a mixture of water (400 mL) and heptane (150 mL) and filtered. The solid was washed again with water, and heptane, to give 6.26 g of 2-cyano-3,3-diphenyl-prop-2-enoic acid as a white solid (yield=87%).

LCMS-ESI: $[M+H]^+$=250 b) tert-butyl N-[2-[(2-cyano-3,3-diphenyl-prop-2-enoyl)amino]ethyl]carbamate

In a 250 mL round bottom flask equipped with magnetic stirring, 2-cyano-3,3-diphenyl-prop-2-enoic acid (2 g, 8.02 mmol) was charged in DCM (50 mL) and DMF (catalytic amount). At 5° C., oxalyl chloride (1.36 mL, 16.05 mmol) were slowly added. The reaction was stirred at RT for 1 h. Solvent and excess of oxalyl chloride were evaporated under reduced pressure to give the acid chloride as a yellow solid.

In a 250 mL round bottom flask equipped with magnetic stirring, N-Boc-ethylenediamine (2.7 g, 16.85 mmol) was charged in DCM (50 mL). Then a solution of the previous acid chloride in DCM (20 mL) was slowly added. The reaction was stirred at RT for 1 h. The reaction mixture was washed with water (3×50 mL), dried over $MgSO_4$ and concentrated to dryness to give 3.19 g of tert-butyl N-[2-[2-cyano-3,3-diphenyl-prop-2-enoyl)amino]ethyl]carbamate as an off-white solid (yield=quantitative).

LCMS-ESI: $[M+H]^+$=292 c) N-(2-aminoethyl)-2-cyano-3,3-diphenyl-prop-2-enamide

In a 250 mL round bottom flask equipped with magnetic stirring, tert-butyl N-[2-[(2-cyano-3,3-diphenyl-prop-2-enoyl)amino]ethyl]carbamate (3.14 g, 8.02 mmol) was charged in DCM (50 mL). At 5° C., TFA (40.5 mL, 529 mmol) was slowly added. The reaction was stirred at RT for 1 h (until end of gas evolution). The reaction mixture was concentrated under vacuum, 25 mL of DCM were added, the resulting solution was washed with NaOH 0.5N (8 mL), dried over $Na_2SO_4$ and concentrated to dryness to give 2.4 g of N-(2-aminoethyl)-2-cyano-3,3-diphenyl-prop-2-enamide as a colorless oil (yield=91%).

LCMS-ESI: $[M+H]^+$=292 d) 2-cyano-N-[2-[3-(2,5-dioxopyrrol-1-yl)propanoylamino]ethyl]-3,3-diphenyl-prop-2-enamide In a 250 mL round bottom flask equipped with magnetic stirring, N-(2-aminoethyl)-2-cyano-3,3-diphenyl-prop-2-enamide (2.33 g, 8.01 mmol) was charged in 60 mL of DCM. 3-(maleimido)propionic acid N-hydroxysuccinimide ester (2.774 g, 10.42 mmol) was slowly added. The reaction was stirred at RT for 18 h, the solution washed with water (50 mL) and dried with $Na_2SO_4$. The crude product was filtered on a silica pad, eluted with DCM, AcOEt and acetone successively. The acetone layer was concentrated under vacuum to give an off-white solid, which was crystallized from a mixture of acetonitrile/iPrOH: 1/4 to give 660 mg of the desired compound. After concentration of the filtrate, a second crystallization from acetonitrile/iPrOH: 1/4 gave 322 mg of a second batch. The two batches were combined and stirred in 20 mL of diisopropylether for 1 h, filtered and dried to give 945 mg of 2-cyano-N-[2-[3-(2,5-dioxopyrrol-1-yl)propanoylamino]ethyl]-3,3-diphenyl-prop-2-enamide as a white solid (yield=26%).

LCMS-ESI: [M+H]+=443

$^1$H NMR 400 MHz, DMSO$d_6$, δ (ppm): 2.27 (2H, tl), 2.79 (2H, dl), 2.97 (2H, dl), 3.58 (2H, tl), 7.01 (2H, s), 7.16-7.5 (10H, m), 7.84 (1H, sl, NH), 8.54 (1H, sl, NH).

$\tilde{\lambda}_{max}$ UV absorbance of Octocrylene in ethanol/DMSO 9/1 was measured at 305 nm and $\tilde{\lambda}_{max}$ UV absorbance of Compound #18 was measured at 293 nm.

Compound #19. 2-cyano-3,3-diphenyl-prop-2-enoate, 2-[2-[3-(2,5-dioxopyrrol-1-yl)propanoylamino]ethylsulfonyl]ethyl ester

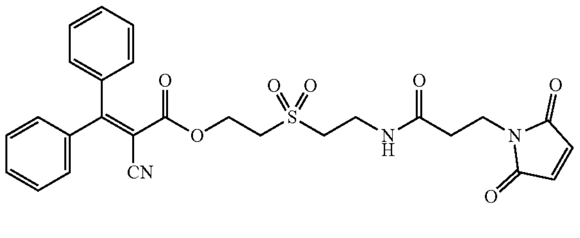 [SMILES: N#CC(C(=O)OCCS(=O)(=O)CCNC(=O)CCN1C(=O)C=CC1=O)=C(c1ccccc1)c1ccccc1]

a) tert-butyl-N-[2-(2-hydroxyethylsulfanyl)ethyl]carbamate

In a 250 mL pear flask equipped with magnetic stirring, to a solution of $Boc_2O$ (2.12 g, 9.69 mmol) in 20 mL of DCM, was added a solution of 2-((2-aminoethyl)-thio)ethanol (1.17 g, 9.69 mmol) in 10 mL of DCM. The mixture was stirred at RT for 30 minutes. Solvent was evaporated under reduce pressure to give 2.21 g of tert-butyl-N-[2-(2-hydroxyethylsulfanyl)ethyl]carbamate as a colorless oil (yield=quantitative). LCMS-ESI: $[M+H]^+$=122 (-Boc)

b) 2-cyano-3,3-diphenyl-prop-2-enoate, 2-[2-(tert-butoxycarbonylamino)ethylsulfanyl]ethyl ester In a 250 mL round bottom flask equipped with magnetic stirring, 2-cyano-3,3-diphenyl-prop-2-enoic acid (2 g, 8.02 mmol) was charged in DCM (100 mL) and DMF (catalytic amount). At +5° C., oxalyl chloride (1.36 mL, 16.05 mmol) was slowly added. The reaction was stirred at RT for 1 h. Solvent and excess of oxalyl chloride were evaporated under reduce pressure to give the acid chloride as a yellow solid.

In a 250 mL round bottom flask equipped with magnetic stirring, tert-butyl-N-[2-(2-hydroxyethylsulfanyl)ethyl]carbamate (2.13 g, 9.63 mmol) was charged in DCM (50 mL), pyridine (973 μl) and a catalytic amount of DMAP. Then a solution of the previous acid chloride in DCM (20 mL) was slowly added. The reaction was stirred at RT for 1 h. The solution was washed with water (3×50 mL), dried over MgSO4 and concentrated under reduce pressure to give 3.49 g of 2-cyano-3,3-diphenyl-prop-2-enoate, 2-[2-(tert-butoxycarbonylamino)ethylsulfanyl]ethyl ester as a colorless oil (yield=96%).

LCMS-ESI: $[M+H]^+$=353 (-Boc)

c) 2-cyano-3,3-diphenyl-prop-2-enoate, 2-[2-(tert-butoxycarbonylamino)ethylsulfonyl]ethyl ester In a 250 mL round bottom flask equipped with magnetic stirring, 2-cyano-3,3-diphenyl-prop-2-enoate, 2-[2-(tert-butoxycarbonylamino)ethylsulfanyl]ethyl ester (3.49 g, 7.71 mmol) was charged in 100 ml of DCM. m-CPBA (3.992 g, 23.13 mmol) was added and the reaction was stirred at RT for 1 h. The DCM solution was washed with $NaHCO_3$, dried over $Na_2SO_4$ and concentrated under reduce pressure to give 3.9 g of 2-cyano-3,3-diphenyl-prop-2-enoate, 2-[2-(tert-butoxycarbonylamino)ethylsulfonyl]ethyl ester as a colorless oil (yield=quantitative).

LCMS-ESI: [M+H]+=385 (-Boc)

d) 2-[2-(2-cyano-3,3-diphenyl-prop-2-enoyl)oxyethylsulfonyl]ethylammonium,2,2,2-trifluoroacetate In a 250 mL round bottom flask equipped with magnetic stirring, 2-cyano-3,3-diphenyl-prop-2-enoate, 2-[2-(tert-butoxycarbonylamino)ethylsulfonyl]ethyl ester (3.55 g, 9.07 mmol) was charged in DCM (100 mL). At +5° C., TFA (6.94 mL, 90.69 mmol) was slowly added. The reaction was stirred at RT for 1 h (until end of gas evolution). The reaction mixture was concentrated under vacuum. 2×25 ml of toluene were added and concentrated to dryness to give 4.5 g of 2-[2-(2-cyano-3,3-diphenyl-prop-2-enoyl)oxyethylsulfonyl]ethylammonium; 2,2,2-trifluoroacetate as a pale yellow oil (yield=99%).

LCMS-ESI: $[M+H]^+$=385 e) 2-cyano-3,3-diphenyl-prop-2-enoate,2-[2-[3-(2,5-dioxopyrrol-1-yl)propanoylamino] ethylsulfonyl]ethyl ester In a 250 mL round bottom flask equipped with magnetic stirring, 2-[2-(2-cyano-3,3-diphenyl-prop-2-enoyl)oxyethylsulfonyl]ethylammonium; 2,2,2-trifluoroacetate (4.5 g, 9.03 mmol) was charged in 50 mL of DCM. 3-(maleimido) propionic acid N-hydroxysuccinimide ester (2.884 g, 10.83 mmol) was slowly added following by DIPEA (15.72 mL, 9.03 mmol). The reaction was stirred at RT for 2 h. The solution was washed with water (50 mL), dried over $Na_2SO_4$ and concentrated under reduce pressure to give a colorless oil (5.8 g). The crude oil was purified on 80 g SiO2 column, solid loading, eluted with gradient from DCM 100% to AcOEt 100% to give 2 g of 2-cyano-3,3-diphenyl-prop-2-enoate, 2-[2-[3-(2,5-dioxopyrrol-1-yl)propanoylamino] ethylsulfonyl]ethyl ester as a white solid (yield=41%).

LCMS-ESI: $[M+H]^+=536$ $^1H$ NMR 400 MHz, $DMSOd_6$, δ (ppm): 2.32 (2H, t), 3.21 (2H, t), 3.39 (4H, m), 3.59 (2H, t), 4.42 (2H, t), 6.99 (2H, s), 7.20 (2H, d), 7.38-7.52 (8H, m), 8.23 (1H, sl, NH).

$\tilde{\lambda}_{max}$ UV absorbance of Octocrylene in ethanol/DMSO 9/1 was measured at 305 nm and $\tilde{\lambda}_{max}$ UV absorbance of Compound #19 was measured at 308 nm.

Compound #20. 3-(2,5-dioxopyrrol-1-yl)-N-[2-[[(3Z)-3-[[4-[(Z)-[4-[2-[3-(2,5-dioxopyrrol-1-yl) propanoylamino]ethylsulfamoylmethyl]-7,7-dimethyl-3-oxo-norbornan-2-ylidene]methyl]phenyl] methylene]-7,7-dimethyl-2-oxo-norbornan-1-yl] methylsulfonylamino] ethyl]propanamide

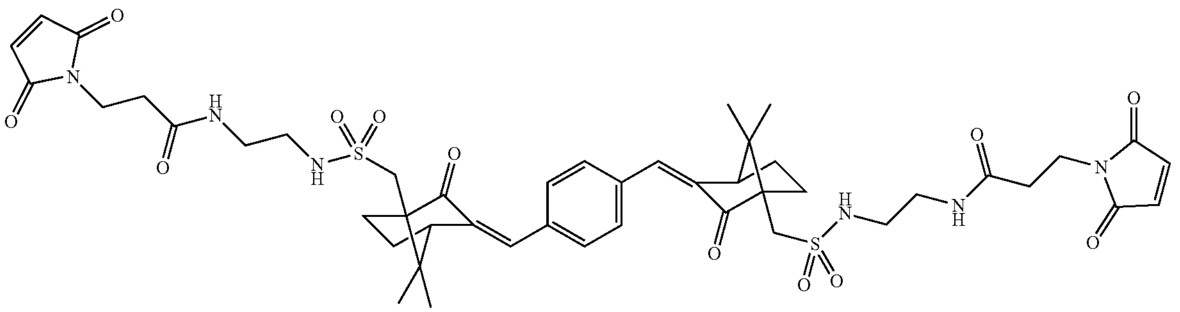 [SMILES: CC1(C)C2CCC1(CS(=O)(=O)NCCNC(=O)CCN1C(=O)C=CC1=O)C(=O)/C2=C\c1ccc(/C=C2\C(=O)C3(CS(=O)(=O)NCCNC(=O)CCN4C(=O)C=CC4=O)CCC2C3(C)C)cc1]

a) Synthesis of tert-butyl N-[2-[[(3Z)-3-[[4-[(Z)-[4-[2-(tert-butoxycarbonylamino) ethylsulfamoylmethyl]-7,7-dimethyl-3-oxo-norbornan-2-ylidene] methyl]phenyl]methylene]-7,7-dimethyl-2-oxo-norbornan-1-yl]methylsulfonylamino]ethyl] carbamate In a 250 mL round bottom flask equipped with magnetic stirring, refrigerant, were charged N-Boc-Ethylenediamine (2.24 g, 14.01 mmol) and TEA (2.7 mL, 20.01 mmol) in THF (60 mL). The solution was cooled at +5° C., and then, ecamsule sulfonyl chloride (4 g, 6.67 mmol) was slowly added. The reaction mixture was stirred at RT for 2 h and then, diluted with water (150 mL). The precipitated was filtered, washed with water to give 5.47 g of tert-butyl N-[2-[[(3Z)-3-[[4-[(Z)-[4-[2-(tert-butoxycarbonylamino) ethylsulfamoylmethyl]-7,7-dimethyl-3-oxo-norbornan-2-ylidene]methyl]phenyl]methylene]-7,7-dimethyl-2-oxo-norbornan-1-yl]methylsulfonylamino]ethyl]carbamate as a pale yellow solid (yield=97%).

LCMS-ESI: $[M+H]^+=747$ (-Boc)

b) N-(2-aminoethyl)-1-[(3Z)-3-[[4-[(Z)-[4-(2-aminoethylsulfamoylmethyl)-7,7-dimethyl-3-oxo-norbornan-2-ylidene]methyl]phenyl]methylene]-7,7-dimethyl-2-oxo-norbornan-1-yl]methanesulfonamide, bis trifluoroacetic salt In a 250 mL round bottom flask equipped with magnetic stirring, was added the previous tert-Butyl carbamate (5.46 g, 6.45 mmol) in DCM (20 mL). TFA (19.7 mL, 257.82 mmol) was added. The reaction mixture was stirred at RT for 1 h, concentrated under reduce pressure to give 9.5 g of a pale yellow solid. The solid was diluted with EtOH (30 mL) and water (10 mL), concentrated under reduce pressure to give 5.67 g the desired compound as a yellow solid (yield=100%).

LCMS-ESI: $[M+H]^+=647$ c) 3-(2,5-dioxopyrrol-1-yl)-N-[2-[[(3Z)-3-[[4-[(Z)-[4-[2-[3-(2,5-dioxopyrrol-1-yl) propanoylamino] ethylsulfamoylmethyl]-7,7-dimethyl-3-oxo-norbornan-2-ylidene] methyl]phenyl]methylene]-7,7-dimethyl-2-oxo-norbornan-1-yl] methylsulfonylamino] ethyl]propanamide In a 250 mL round bottom flask equipped with magnetic stirring, were added the previous TFA salt (3.5 g, 4 mmol) and 3-(Maleimido)propionic acid N-hydroxysuccinimide ester (2.13 g, 8 mmol) in THF (50 mL). Then DIPEA (2.09 mL, 12 mmol) was added and the reaction mixture was stirred at RT for 2 h. The reaction mixture was poured in water (150 mL), extracted with DCM. The organic layer was dried over sodium sulfate, filtered, concentrated under reduce pressure to give a yellow solid (4.2 g). The solid was purified by flash chromatography on 40 g SiO2 column, eluted with gradient DCM 100% to DCM/MeOH 9/1 to give 1.26 g of 3-(2,5-dioxopyrrol-1-yl)-N-[2-[[(3Z)-3-[[4-[(Z)-[4-[2-[3-(2,5-dioxopyrrol-1-yl)propanoylamino]ethylsulfamoylmethyl]-7,7-dimethyl-3-oxo-norbornan-2-ylidene] methyl]phenyl]methylene]-7,7-dimethyl-2-oxo-norbornan-1-yl]methylsulfonylamino]ethyl]propanamide as a white solid (yield=33%).

LCMS-ESI: $[M+H]^+=949.8$ $^1H$ NMR 400 MHz, $DMSOd_6$, δ (ppm): 0.76 (s, 6H), 1.08 (s, 6H), 1.59 (dd, 4H), 2.24 (sl, 2H), 2.34 (t, 4H), 3.03-3.13 (m, 12H), 3.41 (d, 2H), 3.61 (t, 4H), 7.01 (s, 4H), 7.14 (sl, 2H), 7.19 (s, 2H), 7.64 (s, 4H), 8.07 (s, 2H).

$\tilde{\lambda}_{max}$ UV absorbance of Ecamsule in Ethanol/$H_2O$/DMSO 5/3/2 was measured at 341 nm and $\tilde{\lambda}_{max}$ UV absorbance of Compound #20 was measured at 344 nm.

Compound #21. 3-(2,5-dioxopyrrol-1-yl)-N-[3-[4-[4-[4-[3-[3-(2,5-dioxopyrrol-1-yl)propanoylamino] propoxy]-2-hydroxy-phenyl]-6-(4-methoxyphenyl)-1,3,5-triazin-2-yl]-3-hydroxy-phenoxy]propyl] propanamide

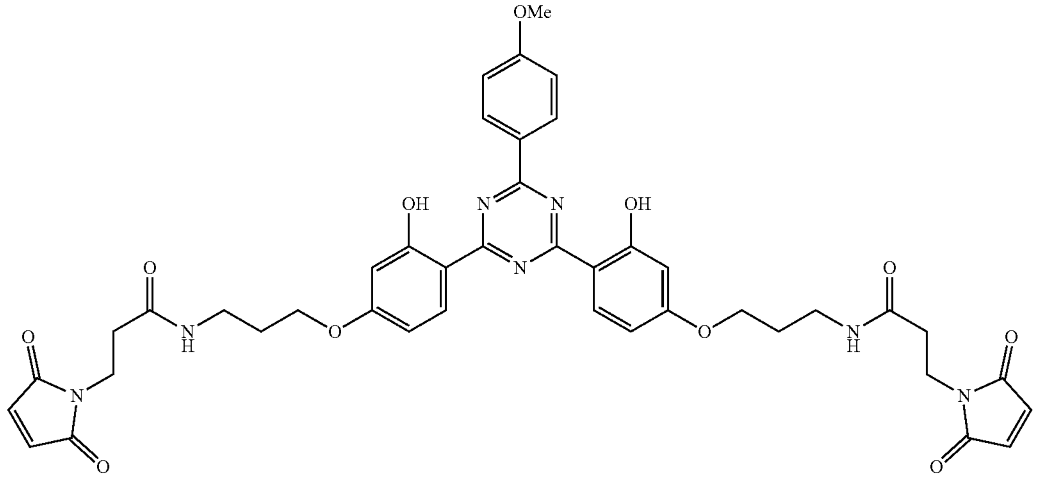 [SMILES: COc1ccc(-c2nc(-c3ccc(OCCCNC(=O)CCN4C(=O)C=CC4=O)cc3O)nc(-c3ccc(OCCCNC(=O)CCN4C(=O)C=CC4=O)cc3O)n2)cc1]

a) N-[3-[3-hydroxy-4-[4-[2-hydroxy-4-[3-tert-butoxycarbonylamino)propoxy]phenyl]-6-(4-methoxyphenyl)-1,3,5-triazin-2-yl]phenoxy]propyl]tert-butoxy carbamate In a 50 mL round bottom flask equipped with magnetic stirring, 4-[4-(2,4-dihydroxyphenyl)-6-(4-methoxyphenyl)-1,3,5-triazin-2-yl]benzene-1,3-diol prepared according to ES 2 730 924 (300 mg, 0.74 mmol) and potassium carbonate (206 mg, 1.49 mmol) were charged in N,N-dimethylformamide (3 mL). 3-(Boc-amino)propyl bromide (370 mg, 1.56 mmol) was added. The reaction mixture was stirred at 50° C. for 6 h. Another 3-(Boc-amino)propyl bromide (176 mg 0.74 mmol) was added and the reaction mixture was stirred at 80° C. for 9 h. After cooling, water (20 mL) was added under stirring; the resulting solid was filtered, washed with water and dried under reduced pressure to give 454 mg of an off-white solid. The solid was dissolved in 3 ml of hot DMF, 3 ml of ACN was added. After cooling and stirring for 30 min, the solid was filtered, washed with ACN to give 340 mg of the desired compound as an off white solid (yield=64%).

b) 5-(3-aminopropoxy)-2-[4-[4-(3-aminopropoxy)-2-hydroxy-phenyl]-6-(4-methoxyphenyl)-1,3,5-triazin-2-yl]phenol, bis hydrochloride In a 15 mL reactor equipped with magnetic stirring, N-[3-[3-hydroxy-4-[4-[2-hydroxy-4-[3-(tert-butoxycarbonylamino)propoxy]phenyl]-6-(4-methoxyphenyl)-1,3,5-triazin-2-yl]phenoxy] propyl]carbamate (273 mg, 0.38 mmol) was charged in dioxane (5 mL). HCl 6N (317 μL, 1.90 mmol) was added and the reaction mixture was stirred at 50° C. for 1 h then at RT for 18 h. The reaction mixture was concentrated under reduced pressure and to give 200 mg of 5-(3-aminopropoxy)-2-[4-[4-(3-aminopropoxy)-2-hydroxy-phenyl]-6-(4-methoxyphenyl)-1,3,5-triazin-2-yl]phenol as an off-white solid (yield quantitative).

LCMS-ESI: $[M+H]^+$=518 c) 3-(2,5-dioxopyrrol-1-yl)-N-[3-[4-[4-[4-[3-[3-(2,5-dioxopyrrol-1-yl)propanoylamino] propoxy]-2-hydroxy-phenyl]-6-(4-methoxyphenyl)-1,3,5-triazin-2-yl]-3-hydroxy-phenoxy]propyl]propanamide In a 15 mL reactor equipped with magnetic stirring, 5-(3-aminopropoxy)-2-[4-[4-(3-aminopropoxy)-2-hydroxy-phenyl]-6-(4-methoxyphenyl)-1,3,5-triazin-2-yl]phenol (197 mg, 0.38 mmol) and diisopropylethylamine (133 μL, 0.76 mmol) were charged in dioxane (3 mL). (2,5-dioxopyrrolidin-1-yl) 3-(2,5-dioxopyrrol-1-yl)propanoate (233 mg, 0.88 mmol) was added. The reaction was stirred at RT for 3 h. The mixture was poured in water (20 mL), the solid was filtered, washed with water to give 200 mg of an off-white solid. The solid was crystallized in AcOH (1 mL), filtered, washed with AcOH, and ACN successively to give 100 mg of 3-(2,5-dioxopyrrol-1-yl)-N-[3-[4-[4-[4-[3-[3-(2,5-dioxopyrrol-1-yl)propanoylamino] propoxy]-2-hydroxy-phenyl]-6-(4-methoxyphenyl)-1,3,5-triazin-2-yl]-3-hydroxy-phenoxy]propyl]propanamide as a brown solid (yield=32%).

LCMS-ESI: $[M+H]^+$=820.3

$^1$H NMR (400 Mhz, DMSO$d_6$, δ (ppm): 1.91 (4H, sl), 2.34 (4H, sl), 3.18 (4H, sl), 3.62 (4H, sl), 3.90 (3H, s), 4.04 (4H, sl), 6.52 (2H, d), 6.65 (2H, sl), 7.01 (4H,$), 7.21 (2H, sl), 8.08 (2H, d), 8.34 (4H, sl), 13.19 (2H, sl)

$\tilde{\lambda}_{max}$ UV absorbance of bemotrizinol in ethanol/benzyl alcohol/DMSO/Phenoxyethanol 63/18/10/9 was measured at 342 nm and $\tilde{\lambda}_{max}$ UV absorbance of Compound #21 was measured at 342 nm.

Compound #22. 3-(2,5-dioxopyrrol-1-yl) N-[2-[2-[2-[2-[4-[4-[4-[2-[2-[2-[2-[3- (2,5-dioxopyrrol-1-yl) propanoylamino]ethoxy]ethoxy]ethoxy]ethoxy]-2-hydroxy-phenyl]-6-(4-methoxyphenyl)-1,3,5-triazin-2-yl]-3-hydroxy-phenoxy]ethoxy]ethoxy]ethoxy] ethyl]propanamide

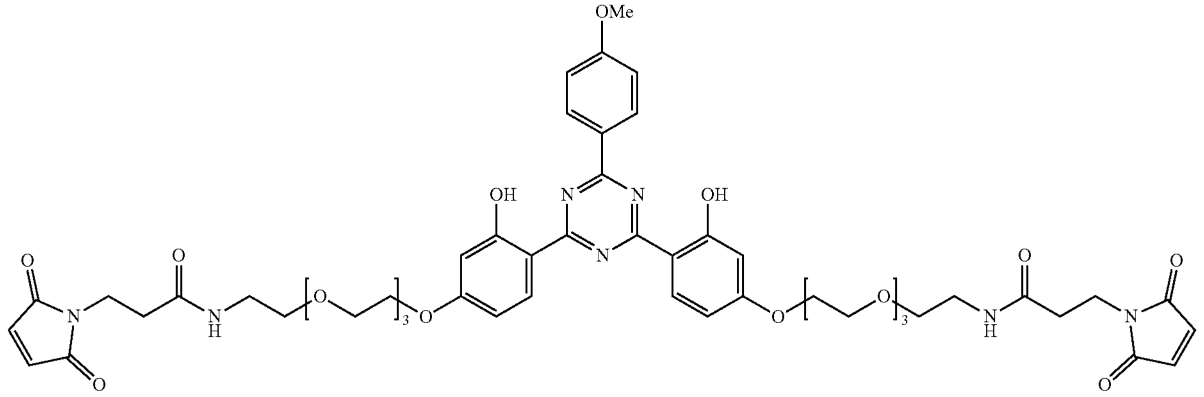

a) tert-butyl N-[2-[2-[2-[2-[4-[4-[4-[2-[2-[2-(tert-butoxycarbonylamino)ethoxy]ethoxy]ethoxy] ethoxy]-2-hydroxy-phenyl]-6-(4-ethoxyphenyl)-1,3,5-triazin-2-yl]-3-hydroxy-phenoxy]ethoxy]ethoxy] ethoxy]ethyl]carbamate In a 50 mL round bottom flask equipped with magnetic stirring, 4-[4-(2,4-dihydroxyphenyl)-6-(4-methoxyphenyl)-1,3,5-triazin-2-yl]benzene-1,3-diol (590 mg, 1.46 mmol) and K2C03 (404 mg, 2.93 mmol) were charged in N,N-dimethylformamide (3 ml). Tert-butyl (2-(2-(2-(2-bromoethoxy)ethoxy)ethoxy)ethyl)carbamate (998 mg 2.93 mmol) was added. The reaction mixture was stirred at 50° C. for 18 h. Water (20 mL) was added; the organic layer extracted with AcOEt, washed with water, brine and dried over $MgSO_4$. The mixture was filtered and the solvent concentrated under reduced pressure. The crude oil was purified by chromatography on SiO2 column, elution from with DCM 100% to DCM/MeOH (93/7) to give 1.58 g of the desired product as yellow oil (yield=quantitative).

b) 5-[2-[2-[2-(2-aminoethoxy)ethoxy]ethoxy] ethoxy]-2-[4-[4-[2-[2-[2-(2-aminoethoxy)ethoxy] ethoxy]ethoxy]-2-hydroxy-phenyl]-6-(4-methoxy-phenyl)-1,3,5-triazin-2-yl]phenol; bis hydrochloride In a 100 mL round flask equipped with magnetic stirring, tert-butyl N-[2-[2-[2-[2-[4-[4-[4-[2-[2-[2-[2-(tert-butoxy-carbonylamino)ethoxy]ethoxy]ethoxy]ethoxy]-2-hydroxy-phenyl]-6-(4-ethoxyphenyl)-1,3,5-triazin-2-yl]-3-hydroxy-phenoxy]ethoxy]ethoxy]ethoxy]ethyl]carbamate (1.40 g, 1.46 mmol) was charged in dioxane (5 mL). HCl 6N (1.22 mL, 7.31 mmol) was added and the reaction mixture was stirred at 60° C. for 1 h then at RT for 18 h. The reaction mixture was concentrated under reduced pressure. The resulting solid was solubilized in MeOH, triturated with Na2SO4, bentonite and charcoal. After stirring for 30 min, the solution was filtered through a pad of celite and concentrated under reduced pressure to give 0.80 g of 5-[2-[2-[2-(2-aminoethoxy)ethoxy]ethoxy]ethoxy]-2-[4-[4-[2-[2-[2-(2-aminoethoxy)ethoxy]ethoxy]ethoxy]-2-hydroxy-phenyl]-6-(4-methoxyphenyl)-1,3,5-triazin-2-yl]phenol, bis hydrochloride as yellow solid (yield=72%).

LCMS-ESI: $[M+H]^+$: 754 c) 3-(2,5-dioxopyrrol-1-yl)-N-[2-[2-[2-[2-[4-[4-[4-[2-[2-[2-[2-[3-(2,5-dioxopyrrol-1-yl) propanoylamino]ethoxy]ethoxy]ethoxy]ethoxy]-2-hydroxy-phenyl]-6-(4-methoxyphenyl)-1,3,5-triazin-2-yl]-3-hydroxy-phenoxy]ethoxy]ethoxy]ethoxy]ethyl]propanamide In a 15 mL reactor equipped with, magnetic stirring, the previous compound (0.80 g, 1.06 mmol) and DIPEA (0.37 mL, 2.12 mmol) were charged in dioxane (6 mL). (2,5-dioxopyrrolidin-1-yl) 3-(2,5-dioxopyrrol-1-yl) propanoate (0.65 g, 2.43 mmol) was added. The mixture was stirred at RT for 3 h. The solution was poured in water (100 mL), extracted with AcOEt. The organic layer was washed with water, brine, dried over Na2SO4, filtered, and concentrated under reduced pressure. The crude oil was purified by chromatography on SiO2 column, eluted with a gradient from heptane 100% 0.28 to acetone 100% to give g of 3-(2,5-dioxopyrrol-1-yl)-N-[2-[2-[2-[2-[4-[4-[4-[2-[2-[2-[2-[3-(2,5-dioxopyrrol-1-yl)propanoylamino]ethoxy]ethoxy]ethoxy]ethoxy]-2-hydroxy-phenyl]-6-(4-methoxyphenyl)-1,3,5-triazin-2-yl]-3-hydroxy-phenoxy]ethoxy]ethoxy]ethoxy]ethyl]propanamide as a yellow oil (yield=25%).

LCMS-ESI: $[M+H]^+$: 1056.4

Example 2. Bioadhesion Tests of Compounds of Formula (I)

The compounds bio adhesion was carried out in solution, for the protein binding, and for the specific binding of sulfhydryl-reactive chemical groups of cysteine. The compounds were mixed either with an equimolar solution of cysteine (two molar equivalent solution of cysteine for the compounds including two maleimides) or an excess of cysteine solution (five or ten times molar compound concentration) and were incubated 1 to 2 minutes in an Ethanol-1×PBS, pH 6.8 solution.

The compound and the compound bound to the cysteine were identified by LC-MSD (Agilent 1260 Infinity II equipped with an Uptisphere strategy C18 or SunFire C18 column) and assayed by HPLC using an Agilent Infinity II Prime UHPLC UV detector system. The separation was achieved by using a gradient phase of water and acetonitrile on an Agilent Poroshell 120 EC-C18 column (3×100 mm, 2.7 μM).

The bio adhesion results of compounds #16 to #20 obtained with an equimolar cysteine solution (two molar equivalent solution of cysteine for the compounds including two maleimides) are shown in Table 1 below.

TABLE 1

Percentage of free and cysteine-bound compound assayed by HPLC in an equimolar cysteine:compound solution.

| Compound | Free compound | Cysteine-bound compound |
|---|---|---|
| compound #16 | 25% | 75% |
| compound #17 | 22% | 78% |
| compound #18 | 27% | 73% |
| compound #19 | 29% | 71% |
| compound #20 | 15% | 85% |

Results of Table 1 show that, in the presence of an equimolar solution of cysteine (two molar equivalent solution of cysteine for compound #20), 71% to 85% of the compound of the invention is bound to cysteine. These results demonstrate that an efficient bioadhesion was obtained with the compounds of the invention.

The bio adhesion results of compounds #16, #18 and #20 obtained with an excess of cysteine in solution are shown in Table 2 below.

TABLE 2

Percentage of free and cysteine-bound compound assayed by HPLC with an excess of cysteine.

| Compound | Free compound | Cysteine-bound compound |
|---|---|---|
| compound #16 | 8% | 92% |
| compound #18 | 1% | 99% |
| compound #20 | 0% | 100% |

Results of Table 2 show that, in the presence of an excess of cysteine, 92% to 100% of the compound of the invention is bound to cysteine. These results also demonstrate that an efficient bioadhesion was obtained with the compounds of the invention.

The invention claimed is:

1. A compound selected from the group consisting of:

2-[4-(diethylamino)-2-hydroxybenzoyl]-benzoic acid, 2-[2-[3-(2,5-dioxopyrrol-1-yl) propanoylamino] ethoxy]ethyl ester;

2-[4-(diethylamino)-2-hydroxy-benzoyl]benzoic acid,

2-[3-(2,5-dioxopyrrol-1-yl)propanoylamino]ethyl ester;

2-cyano-N-[2-[3-(2,5-dioxopyrrol-1-yl)propanoylamino] ethyl]-3,3-diphenyl-prop-2-enamide;

2-cyano-3,3-diphenyl-prop-2-enoate, 2-[2-[3-(2,5-dioxopyrrol-1-yl)propanoylamino]ethylsulfonyl]ethyl ester;

3-(2,5-dioxopyrrol-1-yl)-N-[2-[[(3Z)-3-[[4-[(Z)-[4-[2-[3-(2,5-dioxopyrrol-1-yl) propanoyl amino]ethylsulfamoylmethyl]-7,7-dimethyl-3-oxo-norbornan-2-ylidene]methyl]phenyl]methylene]-7,7-dimethyl-2-oxo-norbornan-1-yl]methylsulfonylamino] ethyl] propenamide;

3-(2,5-dioxopyrrol-1-yl)-N-[3-[4-[4-[4-[3-[3-(2,5-dioxopyrrol-1-yl)propanoylamino]propoxy]-2-hydroxy-phenyl]-6-(4-methoxyphenyl)-1,3,5-triazin-2-yl]-3-hydroxy-phenoxy]propyl]propanamide; and 3-(2,5-dioxopyrrol-1-yl)-N-[2-[2-[2-[2-[4-[4-[4-[2-[2-[2-[2-[3-(2,5-dioxopyrrol-1- yl)propanoylamino]ethoxy] ethoxy]ethoxy]ethoxy]-2-hydroxy-phenyl]-6-(4-methoxyphenyl)-1,3,5-triazin-2-yl]-3-hydroxy-phenoxy]ethoxy]ethoxy]ethoxy]ethyl]propanamide.

2. A composition comprising at least one compound according to claim 1 and at least one excipient.

3. The composition according to claim 2, wherein said composition is a sunscreen composition or a cosmetic composition.

4. Composition according to claim 2, wherein said composition is a pharmaceutical or a veterinary composition.

5. A method of combatting and/or reducing the signs of cutaneous aging, the formation of wrinkles and/or fine lines, skin sagging, loss of firmness, loss of radiance and/or evenness of the complexion, and/or for reinforcing the skin barrier comprising administering a composition according to claim 2 to the skin of a subject.

6. A kit comprising:

a composition as defined in claim 2, a washing composition, and optionally an instruction guide.

7. A method of treating a skin, mucosa, eye cornea, or skin appendage disease or condition comprising applying a veterinary or pharmaceutical composition comprising a compound according to claim 1 and an excipient to the skin, mucosa, eye cornea, or skin appendage of a subject.

8. The method according to claim 7, wherein the skin, mucosa, eye cornea, or skin appendage disease or condition is selected from lipodystrophy, keloid scars, acne, psoriasis, atopic dermatitis, actinic keratosis, rosacea, melasma, melanoma, Merker cell carcinoma, basal cell carcinoma, squamous cell carcinoma, scar treatments, wound healing, alopecia, vitiligo, urticaria, cold sores, impetigo, eczema, rashes dermatitis, ichthyosis, warts, blisters, pruritus, gangrene, bruises, pustules, bacterial skin infections, carbuncles, cellulitis, impetigo, fungal infections, sporotrichosis, fungal nail infections, viral infections, sunburns, lice, scabies, pressure ulcer disinfection, and pressure ulcer healing.

9. A method for reducing photodegradation and/or photoinstability of a pharmaceutical active ingredient or a cosmetic comprising combining a compound according to claim 1 with said pharmaceutical active ingredient or cosmetic.

10. A material comprising a support and at least one compound according to claim 1, said compound being adhered to said support which is a natural or synthetic polymeric support, a natural or synthetic fiber support, a stone, a metal, a plastic, a rubber or a glass support.

11. The compound according to claim 1, wherein the compound is selected from the group consisting of 2-[4-(diethylamino)-2-hydroxy-benzoyl]benzoic acid, 2-[3-(2,5-dioxopyrrol-1-yl)propanoylamino]ethyl ester and 2-[4-(diethylamino)-2-hydroxybenzoyl]-benzoic acid, 2-[2-[3-(2,5-dioxopyrrol-1-yl) propanoylamino]ethoxy]ethyl ester.

* * * * *